United States Patent
Rubinstein et al.

(10) Patent No.: US 11,834,757 B2
(45) Date of Patent: Dec. 5, 2023

(54) HLA HOMOZYGOUS INDUCED PLURIPOTENT STEM CELL (IPSC) LIBRARIES

(71) Applicant: New York Blood Center, Inc., New York, NY (US)

(72) Inventors: Pablo Rubinstein, New York, NY (US); Christopher D. Hillyer, Mamaroneck, NY (US)

(73) Assignee: New York Blood Center, Inc., New York, NY (US)

( * ) Notice: Subject to any disclaimer, the term of this patent is extended or adjusted under 35 U.S.C. 154(b) by 257 days.

(21) Appl. No.: 16/769,028

(22) PCT Filed: Dec. 5, 2018

(86) PCT No.: PCT/US2018/064009
§ 371 (c)(1),
(2) Date: Jun. 2, 2020

(87) PCT Pub. No.: WO2019/113169
PCT Pub. Date: Jun. 13, 2019

(65) Prior Publication Data
US 2021/0230772 A1 Jul. 29, 2021

Related U.S. Application Data

(60) Provisional application No. 62/595,488, filed on Dec. 6, 2017.

(51) Int. Cl.
*C40B 40/02* (2006.01)
*C40B 40/10* (2006.01)

(52) U.S. Cl.
CPC ............. *C40B 40/02* (2013.01); *C40B 40/10* (2013.01)

(58) Field of Classification Search
None
See application file for complete search history.

(56) References Cited

U.S. PATENT DOCUMENTS

| | | | |
|---|---|---|---|
| 6,986,887 B2 | 1/2006 | Lawman et al. | |
| 9,213,999 B2 | 12/2015 | Sakurada | |
| 2004/0091936 A1 | 5/2004 | West | |
| 2013/0276154 A1 | 10/2013 | West | |
| 2017/0044500 A1* | 2/2017 | Cooper | A61K 39/001171 |
| 2017/0304417 A1* | 10/2017 | Kawamoto | A61K 39/0011 |

FOREIGN PATENT DOCUMENTS

| | | |
|---|---|---|
| WO | 2007/047894 A2 | 4/2007 |
| WO | 2010/148334 A2 | 12/2010 |

OTHER PUBLICATIONS

International Search Report and Written Opinion, dated Apr. 16, 2019, for International Application Serial No. PCT/US2018/064009 filed Dec. 5, 2018.
De Rham et al., Potential and Limitation of HLA-Based Banking of Human Pluripotent Stem Cells for Cell Therapy. Journal of Immunology Research, vol. 2014, No. 2; p. 2 (2014).

(Continued)

*Primary Examiner* — Christian C Boesen
(74) *Attorney, Agent, or Firm* — K&L Gates LLP; Louis C. Cullman; Michelle Glasky Bergman

(57) ABSTRACT

The present specification provides libraries of HLA homozygous induced pluripotent cell lines.

20 Claims, 2 Drawing Sheets

(56) References Cited

OTHER PUBLICATIONS

Gonzalez-Galarza et al., Allele frequency net 2015 update: new features for HLA epitopes, KIR and disease and HLA adverse drug reaction associations. Nucleic Acid Research, vol. 28, D784-D788 (2015).
Duquesnoy et al., Int. J. Immunogenetics, vol. 0, pp. 1-6 (2012).
Maiers et al., High resolution HLA alleles and haplotypes in the United States population. Hum Immunol., vol. 68, pp. 779-788 (2007).
Rubinstein et al., Histocompatibility and Immunogenetics in Cord Blood Transplantation. Biol. Res., vol. 43, pp. 339-345 (2010).
Revazova et al., HLA homozygous stem cell lines derived from human parthenogenetic blastocysts. Cloning. Stem. Cells, vol. 10(1), pp. 11-24 (2008).
Craig et al., Generating an iPSC Bank for HLA-Matched Tissue Transplantation Based on Known Donor and ecipient HLA Types. Synthesis, vol. 11, pp. 147-152 (2012).
Umekage M et al. "Overview: an iPS cell stock at CiRA" Inflammation and Regeneration Sep. 2, 2019;39:17. doi: 10.1186/s41232-019-0106-0. eCollection 2019.
Ichise H et al. "NK Cell Alloreactivity against KIR-Ligand-Mismatched HLA-Haploidentical Tissue Derived from HLA Haplotype-Homozygous iPSCs" Stem Cell Reports 9:583-867, 2017.

\* cited by examiner

HLA HOMOZYGOUS INDUCED PLURIPOTENT STEM CELL (IPSC) LIBRARIES

CROSS-REFERENCE TO RELATED APPLICATIONS

This application is a 35 U.S.C. 371 national phase entry of PCT/US2018/064009, filed Dec. 5, 2018, which claims the benefit of U.S. provisional patent application 62/595,488, filed Dec. 6, 2017; the entire contents of which are each incorporated by reference herein.

BACKGROUND

The ability to culture and differentiate stem cells has offered great promise for the repair or replacement of damaged or defective tissues and organs that has yet to be realized. The field of stem cell therapy originally grew out of research on embryonic stem cells. The development of induced pluripotent stem cells (iPSC) greatly expanded access to stem cells and reduced ethical concerns over their use. One remaining impediment to clinical use of iPSCs, and cells differentiated from them, in the treatment of diseases and injuries is the potential for immunological rejection of iPSC-derived tissue.

One potential solution is autologous donation. However, if there is a genetic component to the condition being treated, the autologous iPSCs would then carry the same defect(s). This would not be a concern in conditions for which a gene therapy was available—and indeed that is one intended application of stem cell technology—but there are others where no genetic therapy has been developed and still others that are complex multigenic conditions not amenable to therapy by correction of the underlying genetic defect(s). Another drawback to autologous donation is the necessity of starting from scratch for every patient. The need to obtain tissue from a patient and induce pluripotency before initiating the steps of the actual treatment adds to the time before treatment can commence and introduces opportunities for mishap, misadventure, and failure of the process.

Allogeneic donation at need is also possible, but finding an immunologically compatible donor can be difficult and the potential need for extensive immunosuppression is undesirable. And like autologous donation, this approach also suffers from the need to start from the very beginning of the process each time. Banking iPSC lines could address this latter issue, but merely taking cells from willing donors will exacerbate the problem of finding an immunologically compatible donor, at least without assembling a massive bank of cells with diverse tissue types. Some have proposed knocking out major histocompatibility complex (MHC) genes to reduce or avoid immunological rejection, but this results in more highly manipulated cells which some will consider undesirable, especially if further genetic manipulation will be part of the therapeutic use. Also the cell will not be able to participate in normal immunophysiology.

Thus, there exists a need for off-the-shelf iPSC lines that are minimally manipulated, are capable of normal immunophysiologic interactions, and can be used in a substantial portion of a patient population. Herein disclosed is such an iPSC library.

SUMMARY

The herein disclosed embodiments include libraries of HLA (or MHC) homozygous induced pluripotent stem cell (iPSC) lines and methods for the production of such cell lines and assembly of such libraries. The individual HLA homozygous iPSC lines of the libraries are useful for providing cells for transplantation into HLA-matched recipients. The iPSC line cells can be differentiated into a desired cell type or tissue prior to transplantation. A library itself provides a ready source of HLA-matched donor cells for a substantial portion of a target, service, or recipient population, obviating the need to seek an individual donor at the time the need for a donation arises. By comprising HLA-homozygous cell lines the library can serve a much greater proportion of the target, service, or recipient population than if it the iPSC cell lines were heterozygous.

Some embodiments constitute a library of from at least 15, 20, 25, 30 . . . or 100 to 1000, or any range bounded by integers therein, iPSC lines wherein the iPSC lines are homozygous for at least a selected set of MHC loci, and wherein each iPSC line in the library comprises a different HLA (MHC) haplotype or a different combination of HLA (MHC) haplotype and ABO blood type. It is preferred the iPSC lines be ABO type O, but in some embodiments multiple iPSC lines may possess the same HLA (MHC) haplotype but different ABO types. In some embodiments the donor cell is not ABO type O, but the iPSC line is genetically engineered to be type O. In some embodiments the selected set of comprises specifically HLA loci, while other embodiments comprise other MHC loci instead or in addition. In some embodiments the selected set of comprise HLA-A, -B, and -DR. In some embodiments the selected set of MHC loci comprises at least one locus from telomeric side of the major histocompatibility complex or at least one locus from the centromeric side of the major histocompatibility complex, or both, in addition to or instead of the previously indicated loci. In some embodiments the selected set of loci comprises one or more of HLA-C, -DQ, or DP in addition to or instead of the previously indicated loci. In some embodiments the selected set of loci comprises one or more of MICA or MICB in addition to or instead of the previously indicated loci. In some embodiments some or all of the iPSC lines are autozygous for the selected set of MHC loci.

In some embodiments the library comprises a certain proportion or percentage of the most frequent haplotypes in a defined or reference population or subpopulation. In various aspects of these embodiments the library may comprise, for example, all haplotypes that occur at a frequency >2%, >3% or >4% in the defined population, or ≥50%, ≥60%, ≥70%, ≥80%, ≥90%, or ≥95% of all haplotypes occurring at a frequency of >1%, >0.9%, >0.8%, >0.7%, >0.6%, >0.5%, >0.4%, >0.3%, >0.2%, >0.1%, >0.09%, >0.08, >0.07%, >0.06% or >0.05% in the defined population, or combinations thereof. In various embodiments the reference population is defined by geographic origin, geographic location, ethnic background, or a combination thereof.

In some embodiments at least 10 of the iPSC lines in the library have a haplotype listed in Table 1

TABLE 1

| HLA-A* | HLA-B* | HLA-DRB1* |
|---|---|---|
| 01:01 | 08:01 | 03:01 |
| 03:01 | 07:02 | 15:01 |
| 02:01 | 44:02 | 04:01 |
| 02:01 | 07:02 | 15:01 |
| 29:02 | 44:03 | 07:01 |
| 02:01 | 15:01 | 04:01 |
| 01:01 | 57:01 | 07:01 |

TABLE 1-continued

| HLA-A* | HLA-B* | HLA-DRB1* |
|---|---|---|
| 03:01 | 35:01 | 01:01 |
| 02:01 | 40:01 | 13:02 |
| 30:01 | 13:02 | 07:01 |
| 02:01 | 08:01 | 03:01 |
| 02:01 | 57:01 | 07:01 |
| 24:02 | 07:02 | 15:01 |
| 11:01 | 35:01 | 01:01 |
| 33:01 | 14:02 | 01:02 |
| 23:01 | 44:03 | 07:01 |
| 01:01 | 07:02 | 15:01 |
| 02:01 | 15:01 | 13:01 |
| 02:01 | 13:02 | 07:01 |
| 31:01 | 40:01 | 04:04 |
| 25:01 | 18:01 | 15:01 |
| 02:01 | 44:03 | 07:01 |
| 02:01 | 44:02 | 13:01 |
| 02:01 | 44:02 | 01:01 |
| 01:01 | 08:01 | 15:01 |
| 03:01 | 07:02 | 01:01 |
| 02:01 | 44:02 | 15:01 |
| 02:01 | 51:01 | 11:01 |
| 26:01 | 38:01 | 04:02 |

In some embodiments the homozygous haplotypes expressed by the iPSC lines comprise at least those on the above list.

In some embodiments the iPS cell lines are derived from cord blood. In some embodiments the iPS cell lines are derived from CD34+ cord blood cells. In some embodiments the iPS cells are reprogrammed by, and initially express, Oct-4, Sox-2, Klf-4, and c-Myc.

In some embodiments homozygous donors are identified by screening random blood donors or random persons being tissue typed for other reasons. In other embodiments homozygous donors are identified by screening volunteers from a general population. In still other embodiments homozygous donors are identified by screening volunteers from a population likely to have a higher frequency of homozygosity or a higher frequency of a particular desired haplotype.

Some embodiments constitute methods of producing a library of HLA homozygous iPSC. Such methods can comprise screening whole blood, preferably cord blood for MHC homozygosity according to the parameters described above, for genetic, cytogenetic and other genomic and chromosomal abnormalities, and for donor history and markers of exposure to infectious diseases. Such methods can further comprise isolating white blood cells from the screened units of blood that were negative for the genetic defects and exposure to the infectious diseases and positive for the homozygosity, causing the white blood cells to express Oct-4, Sox-2, Klf-4, and c-Myc to form iPS cells, and culturing and cloning the iPSC to produce a population of cloned iPS cells homozygous for the selected set of MHC loci. Such methods can further comprise characterizing the genotype of the iPSC by typing additional MHC loci such as class I, II and III genes and including the A,B,C and DR loci if they were not part of the initial selected set. Such methods can further include screening the cells from iPSC clones for the presence of chromosomal aberrations and evidences of genetic instability, and cryoprotecting and storing the cloned population of iPSC.

In aspects of the above methods the causing step can include using vectors capable of inducing the target white blood cells to express the exogenous transcription factors Oct-4, Sox-2, Klf-4, and c-Myc. Such vectors can be an episomal, viral, or a non-viral vector and the specific transcription factors Oct-4, Sox-2, Klf-4, and c-Myc are encoded as DNA, RNA, or protein. Such methods can further comprise isolating hematopoietic CD34+ cells from the cord blood prior to the causing step. Storing can comprises cryogenically preserving the iPSC at temperatures below −150° C.

Some embodiments constitute a library produced by the forgoing methods.

Some embodiments constitute methods for providing differentiated cells derived from an iPSC library to a subject in need thereof. Such methods can comprise determining the HLA haplotype for HLA-A, -B, -C and -DR of the subject; selecting an iPSC line from the library which contains a match at all of HLA-A, -B, -C, and -DR loci with the subject's HLA phenotype for those loci; differentiating the iPSC into a cell type needed by the subject; and providing the differentiated cells to the subject. Such methods can further comprise expanding and fully differentiating the iPS cells into a differentiated cell type (e.g., neural cells, myocardial muscle cells, insulin-producing cells, etc.) and ensuring the disappearance of the pluripotent cells and inducing vectors, as well as the genetic stability of the differentiated cells. In some embodiments providing the differentiated cells to the subject comprises providing the differentiated cells to the subject's medical provider.

In one embodiment the library of HLA homozygous induced pluripotent stem cell (iPS) lines comprises at least 20 iPS cell lines homozygous for alleles at HLA-A, -B, -DR, MICA and MICB loci, each cell line expressing a different homozygous haplotype. In a further aspect of this embodiment each of the iPS cell lines has been reprogrammed into pluripotentiality by means of non-endogenous transcription factors.

In one embodiment the library of HLA homozygous induced pluripotent stem cell (iPS) lines comprises at least 20 iPS cell lines homozygous for alleles at HLA-F and -DPB3 loci, each cell line expressing a different homozygous haplotype, wherein the haplotype difference can be at an HLA-A, -B, or -DR locus. In a further aspect of this embodiment each of the iPS cell lines has been reprogrammed into pluripotentiality by means of non-endogenous transcription factors.

DESCRIPTION

Figure 1:
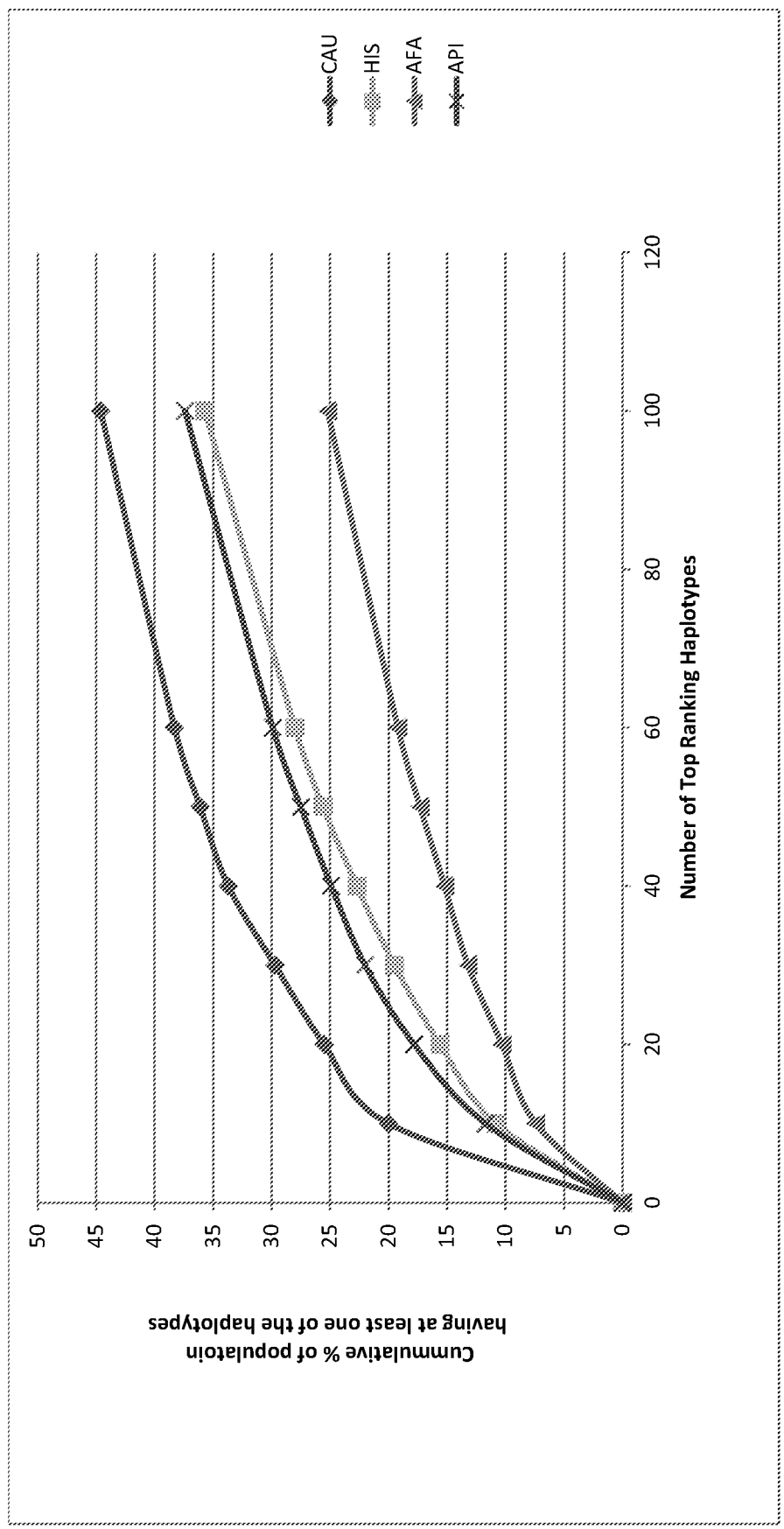
FIG. 1 depicts the cumulative percentage of the population possessing the most frequent haplotypes for four US subpopulations (Caucasian, Hispanic, African-American, and Asian or Pacific Islander) based on the US National Marrow Donor Program data.

Embodiments disclosed herein relate to libraries (also called arrays) of induced pluripotent stem cell (iPSC) lines that are homozygous for at least major histocompatibility (MHC) antigens HLA-A, HLA-B, and HLA-DR, or at least HLA-A, HLA-B, HLA-C, and HLA-DR. These loci are the most important to match between donor and recipient to gain immunocompatibility and to facilitate engraftment of transplanted tissue. In alternative embodiments, the library of iPSC lines can be characterized of defined as being homozygous at loci near either end of the major histocompatibility complex (MHC). For example, the constituent cell lines can be homozygous for at least one or more loci toward the telomeric side of the MHC, such as HLA-F, MICE, HLA-90, MICG, HLA-G, MICF, HLA-K, HLA-U, or HLA-A, and for at least one of more loci toward the centromeric side of the MHC, such as HLA-DQA1, HLA-DQB1, HLA-DQB3, HLA-DQA2, HLA-DQB2, HLA-DOB, HLA-Z, HLA-DMB, HLA-DMA, HLA-DOA, HLA-DPA1, HLA-DPB1, HLA-DPA2, HLA-DPB2 or HLA-DPB3. In further embodiments according to either alternative, the iPSC lines are also homozygous at MICA (MHC class I chain-related protein A) and/or MICB (MHC class I chain-related protein B).

Although the iPSC lines may be selected or defined according to the loci indicated above, in some embodiments the cell lines will be characterized at additional loci: for example class I loci such as HLA-C, HLA-E, HLA-F, HLA-G, HLA-H, HLA-J, HLA-K, HLA-L, HLA-P, or HLA-V; and/or class II loci such as DRA, DRB2-DRB9, DQA1, DPA1, DPA2, DPB1, DPB2, DMA, DOA, or DOB; and/or MICA or MICB; and/or class III loci such as C2, C4A, C4B, and CFB (the C-3-activating complement components), CYP21, and TNX. In some embodiments, the iPSC lines are homozygous at one or more of these additional loci. In some embodiments homozygosity at one of more of these loci is a selection criterion for inclusion in a library or part of the minimal definition of the iPSC lines in the library.

In some embodiments the donors and resulting iPSC lines are not merely homozygous for the specified haplotype, but autozygous. That is, the homozygosity reflects inheritance of both haplotypes from the same common ancestor as can result from consanguineous mating. Autozygosity will insure a greater degree of identity between the two haplotypes than random homozygosity which allows for greater accumulation of mutation and greater likelihood of meiotic cross-over causing non-identity at unevaluated loci. In clinical genetics consanguineous unions are those between persons related as second cousins or closer or having an inbreeding coefficient (the proportion of loci at which the offspring is expected to receive identical alleles from both parents) ≥0.0156.

It is preferred that the donors of the homozygous cells be from ABO blood group O (so-called universal blood donor type), It is also preferred that the donors of the homozygous cells be male to avoid potential reactivation of the one X-chromosome that is normally inactivated in females. Thus in various embodiments at least 50, 60, 70, 80, 90, 95, or 100 percent of the iPSC lines in a library are derived from blood group O donors, from male donors, or from male, blood group O donors.

By being homozygous, the cell lines express only one antigen for each of the loci and thus there is only one antigen per locus to match to the potentially two expressed antigens per locus of prospective recipients. Or from the perspective of the prospective recipients, they need only find an iPSC line in the library that expresses either of the antigens they express at each locus. This greatly increases the likelihood of finding a match as compared to matching with heterozygous donors, in which case one is attempting to match two antigens at each locus. For a hematopoietic graft using neonatal cells, the National Cord Blood Program estimates that to provide acceptable matches for 80-90% of the US population, an inventory of 150,000 (random, primarily heterozygous) cord blood units would be needed. By contrast, based on data from the National Marrow Donor Program, a library of homozygous iPSC lines representing the 1000 haplotypes most commonly encountered in the US Caucasian population would provide a haplotype match for over 80% of that population. The likelihood of any random prospective recipient finding a compatible cell line in the library is increased by the inclusion of HLA types or alleles, and HLA-haplotypes, which occur more frequently in the prospective recipient population. The likelihood of any random prospective recipient finding a compatible cell line in the library is also increased by the inclusion of ever larger and more diverse set of iPSC lines. However, a point of diminishing returns is reached both with respect to the cost of assembling and maintaining the library, and to the difficulty of finding (homozygous) haplotypes representing ever rarer HLA types or haplotypes. No such library of practical size will ever contain a matching cell line for every possible prospective recipient.

The assembly of a library of homozygous cells is facilitated by routine access to HLA-typed tissue, although a dedicated screening program could be used instead of, or in conjunction with, programs conducted for independent reasons. Example 5 below describes assembling a library from cord blood units from the National Cord Blood Program of the New York Blood Center. However any tissue typing lab, such as those associated with organ transplant centers, will in the course of their work, come across persons who are homozygous at their HLA loci. With proper consent, already donated blood, or blood or other tissue specifically donated for this purpose, can be used as source material for the generation of iPSC lines.

The art of tissue typing has evolved since the first descriptions in 1958 of what became known as human leukocyte antigens (HLA). Initially typing was done serologically using polyclonal antisera from multitransfused patients and multiparous women. Over time, monoclonal antibodies were also adopted and now most typing is done at the genetic level, utilizing PCR, DNA hybridization, and sequencing. As data accumulated, it became clear that some serologic reactivities arose from allelic variation at the same locus while other reactivities reflected independent loci. As more specific serologic reagents became available, more serologic types were identified and some types "split"; for example, A9 became A23 and A24 and the A9 designation ceased to be used. Not surprisingly, the use of terminology has evolved along with our understanding and technology and usage over time is not consistent. We shall observe the following conventions:

HLA [antigen] identities defined by serologic reactivity shall be referred to as HLA types, and in some contexts as serologic types or serotypes, or phenotypes.

HLA [antigen] identities defined by DNA sequence shall be referred to as alleles or genotypes.

A group of alleles or serotypes encoded on a single chromosome shall be referred to as a haplotype.

A group of alleles or serotypes encoded at one or more loci, but on both members of the chromosome pair, shall be referred to as a tissue type.

It should be understood that some genotypic differences are silent with respect to amino acid sequence and that others, while giving rise to a difference in amino acid sequence, do not generate a difference in serologic reactivity or, more to the point, in clinical immunoreactivity. Thus, such allelic variation is phenotypically silent. Conversely, some genotypic differences encode differences in amino acid sequence that can give rise to clinical immunoreactivity despite falling within the same traditional HLA type.

Depending on the particular use to which the iPSC will be put, such allelic differences in immunogenicity may or may not require consideration in determining a match.

The current convention for the naming of HLA alleles, set by the WHO Nomenclature Committee for Factors of the HLA System, are based on the results of typing at the DNA sequence level are summarized as follows:

Exemplary HLA allele name: HLA-A*02:101:01:02N

Locus designation: The first field of the name refers to the HLA locus (e.g., HLA-A) which is followed by an asterisk (*) separating it from the allele designation.

Allele designations: each HLA allele name has a unique number, composed of up to four sets of two or three digits separated by colons. The length of the allele designation (number of two-digit or three digit sets) is dependent on the sequence of the allele and that of its nearest relative.

All alleles receive at least a four digit name, including the first two sets of digits (fields) following the asterisk, longer names are only assigned when necessary. The digits in the first field (i.e., 02) describe the type, which often corresponds to the serological antigen encoded by the allele at the locus (the allotype). The second field lists the subtypes, numbered in the order in which the respective DNA sequences have been determined (i.e., 101). DNA sequences of alleles whose numbers differ in the first two fields must differ in ways that change the amino acid sequence of the encoded protein. Although not strictly proper, it is a common practice to omit the colon between the type and subtype fields when the subsequent fields are not used. (02:101 and 02101 refer to the same allele).

Alleles that differ only by synonymous nucleotide substitutions (also called silent or non-coding substitutions) within the coding sequence are distinguished by the use of a third set of digits (i.e., 01).

Alleles that only differ by sequence polymorphisms in the introns, or in the 5' or 3' untranslated regions that flank the exons and introns, are individualized by the use of a fourth set of digits (i.e., 02).

In addition to the unique allele number, optional suffixes may be added to a particular allele to indicate variations in its expression status. Thus, alleles shown NOT to be expressed—'Null' alleles—have the suffix 'N'. Alleles that have been shown to be alternatively expressed may have the suffix 'L' (low cell surface expression), 'S' ('soluble' encodes a secreted protein not present at the cell surface), 'C' (is expressed at the 'cytoplasm' but not at the cell surface), 'A' ('aberrant' when actual expression is in doubt) and 'Q' (when the expression is 'questionable' because it resembles mutations seen in other alleles that have abnormal expression. Because of the practical importance of the change in expression, particularly with Null alleles, the phenotype should be defined when transplantation is contemplated.

The closely-linked alleles of the HLA genes form "haplotypes" that remain together, segregating as a block in meiotic divisions, although rarely (frequency ~0.8% between HLA-A and -B; and ~1% between HLA-B and -DRB1) the HLA loci in a haplotype become separated by a cross-over event leading to genetic recombination. Despite these crossovers, some of the alleles at different HLA loci "associate" with each other so that their frequency together in the same haplotype is higher, or much higher, than should be expected given their respective population frequencies. This phenomenon has been designated "Linkage Disequilibrium" (LD). Because the frequency of some specific HLA haplotypes is much higher than expected from the frequency of the respective alleles, the frequencies of any haplotypes that include one of the alleles involved in such a preferential association—but not the others—are lower than expected under the assumption of random association of alleles into HLA haplotypes. Many of the alleles at HLA loci, and the preferential haplotypes they integrate, have very different frequencies in different ethnic groups within populations. This has contributed to the disproportionately higher access to matched unrelated donors for patients of majority ethnic groups in the US. Because of the close distance between the HLA loci and low recombination rate, and other causes not specifically understood, LD persists despite the existence of recombination within the HLA haplotypes and includes specific alleles of other gene loci located between and outside the "classic" Class I and Class II loci. In general, numerically, LD is defined in relation to the quantity "D":

$$D_{AB} = p_{AB} - p_A\, p_B$$

which is the difference between the frequency of a haplotype carrying both alleles A and B at the two linked loci (pAB) and the product of the frequencies of those alleles (pA and pB). Consequently, there is no disequilibrium when DAB=0, and maximum disequilibrium (DAB=1) when at least one of the four possible haplotypes (AB, Ab, aB, ab) does not occur. It has been shown that, for many HLA haplotypes, much of their population frequency is due to LD, and that it extends to further loci in the adjacent areas of the chromosome. In terms of the array of HLA-homozygous iPSC lines disclosed here, LD contributes two critical advantages, a) it allows for relatively easier assembly of iPSC lines, each with an HLA haplotype of comparatively high frequency, which permits a large fraction of the population to have access to matched tissues derived from relatively few iPSC lines, and b) it provides a high level of certainty that alleles at additional MHC loci in the haplotype (including non-classical HLA genes and MICA) are also homozygous, in LD with the HLA loci and very likely also matched to any recipients who are matched for the classical HLA loci.

Numerical aspects of linkage disequilibrium are presented below in Table 2, refer to allele and haplotype frequencies of the three most frequent HLA haplotypes in US Caucasoids.

TABLE 2

Linkage Disequilibrium: the three most frequent Caucasoid HLA Haplotypes, the HLA alleles involved and their respective ranked frequencies HAPLOTYPE: HLA-A*01:01; B*08:01; DRB1*03:01 - [RANKED: 1$^{st}$]

| Allele | Frequency | (Rank) |
|---|---|---|
| A*01:01 | 0.172 | (2) |
| B*08:01 | 0.125 | (2) |
| DRB1*03:01 | 0.129 | (3) |

Haplotype Frequency = 0.074; Expected (pA × pB × pDRB1) = 0.0028 (26-fold increase)

HAPLOTYPE: HLA-A*03:01; B*07:02; DRB1*15:01 - [RANKED: 2$^{nd}$]

| Allele: | Frequency | (Rank) |
|---|---|---|
| A*03:01 | 0.143 | (3) |
| B*07:02 | 0.140 | (1) |
| DRB1*15:01 | 0.144 | (1) |

Haplotype Frequency = 0.035; Expected (pA × pB × pDRB1) = 0.0029 (12-fold increase)

HAPLOTYPE: HLA-A*02:01; B*44:02; DRB1*04:01 - [RANKED 3$^{rd}$]

TABLE 2-continued

Linkage Disequilibrium: the three most frequent
Caucasoid HLA Haplotypes, the HLA alleles involved and
their respective ranked frequencies

| Allele: | Frequency | (Rank) |
|---|---|---|
| A*02:01 | 0.296 | (1) |
| B*44:02 | 0.090 | (3) |
| DRB1*04:01 | 0.091 | (5) |

Haplotype Frequency = 0.026; Expected (pA × pB × pDRB1) = 0.0024 (11-fold increase)

Thus, most of the population frequency of the most frequent haplotypes is due to LD and not to the high gene frequencies of the specific alleles. The other benefit of LD pursuant to using HLA homozygous grafts comes from the LD with, and homozygosity of, other genes in the MHC region of chromosome 6, including MICA and MICB, as well as non-classical HLA loci and many other genes. Non-HLA immune rejection due to humoral anti-MICA antibodies, for instance, is a distinct clinical problem in kidney transplantation. Products of some non-classical HLA loci appear to influence immune regulation, others are important in regards defining the modulation of NK (natural killer) cell function and some were shown to increase the risk and severity of graft vs host complications in hematopoietic stem cell transplantation.

In determining a match, one generally will be matching the tissue type (both alleles at each of the loci under consideration) of the prospective recipient with the haplotypes (single alleles at each of the loci under consideration) present in the library. It is not necessary to match at the level of haplotype (though it would make matching at additional MHC loci more likely and thus can be preferable) and haplotyping prospective recipients is not routinely done as it requires tissue typing multiple blood relatives or specific cloning and sequencing procedures. Indeed, because of linkage disequilibrium most matches will in fact share a common haplotype. As long as the prospective recipient's tissue type includes a serotype or allele at each locus that corresponds to the allele at the 3 (or 4 or 5 or more) specified loci in the haplotype then there is a match. In some embodiments matching is evaluated at the level of serotype (also referred to as antigen-level resolution matching); for example a haplotype containing an A*02:01 allele would be considered a match at the HLA-A locus for any prospective recipient expressing any HLA-A2 antigen. However, as more precise typing has become ever more common this has become an increasingly disfavored practice, though not entirely abandoned. In other embodiments matching is evaluated at the level of genotype (also referred to as allele-level resolution matching); for example a haplotype containing an A*02:01 allele would be considered a match at the HLA-A locus for only a prospective recipient whose tissue type included an A*02:01 allele; or in a variation of these embodiments, alleles differing only by genetically or immunogenically silent polymorphisms are also considered a match. In some embodiments matching is evaluated at the level of serotype for one locus and at the level of genotype at another locus; for example using antigen-level resolution match for HLA-A and -B and allele-level resolution matching for DR. Clinical practice has largely moved to allele-level resolution matching, and it is generally associated with superior results in avoiding rejection. However, it should not be ignored that tissue and organ transplantation was successfully practiced before allele-level resolution was even possible. Thus while the proportion of a population that would be served by a particular library might be calculated based on allele-level resolution, actual clinical practice may proceed with less stringent matching—or even allow some mismatch—depending on the particular application and other considerations that may arise in a particular case. This would tend to increase the usefulness of any particular iPSC library.

The decision whether to use allele-level (genotype) or antigen-level (serotype) resolution in evaluating matching can be influenced by the susceptibility of the organ or tissue to be repaired to rejection, and thus the necessity for more precise matching; for example kidney tissue is more susceptible to rejection than heart tissue which is more susceptible than liver tissue. It can also be influenced by whether the location where the transplanted tissue is to be placed enjoys immune privilege; for example foreign antigens placed in the brain or eye are generally non-immunogenic. They are, however, still susceptible to immune attack if a response to the antigen is induced elsewhere in the body. The more susceptible the transplanted tissue is expected to be to rejection, the greater the impetus to seek an allele-level match. However, while more stringent matches are generally expected to provide better results, one may nonetheless decide to proceed with an antigen-level match if an iPSC providing an allele-level match is not available. The decision can also be influenced by the degree of immunosuppression, if any, that would be expected to be required to support engraftment and maintenance of the transplanted tissue and the acceptability of the immunosuppressive regiment for the particular prospective recipient. The least immunosuppression expected to be needed—other things being equal—is preferred. In some instances the decision to seek an allele-level match or accept an antigen level match is made on a locus by locus basis.

If a perfect match at the desired level of resolution for the number of loci being considered cannot be obtained, one can still consider going forward with a mismatch. In some embodiments matching includes consideration of the HLA-C allele or type, but as rejection is only infrequently attributed to reactions against HLA-C, a mismatch at that locus can be deemed acceptable in some instances. The presence of various defined antibody epitopes on the HLA molecule can also be considered so as to minimize the prevalence of antigenic and immunogenic sites on the mismatched HLA molecule as compared to those present in the tissue type of the prospective recipient (See EpiPedia of HLA posted on the International HLA Epitope Registry website: wwwdotepregistrydotcomdotbr, which can be accessed by changing "dot" to "."). The HLA Epitope Registry is also described in Duquesnoy, R J et al., *Int J Immunogenetics* 2012, 0, 1-6. Additional tools to understand and evaluate the presence of antibody epitopes are available on the internet including: HLAMatchmaker (wwwdotepitopesdotnet), EpVix (wwwdotepvixdotcomdotbr), and the epitope frequency search function (wwwdotallelefrequenciesdotnet/hlaepitopes/hlaepitopesdotasp) at the Allele Frequency Net Database (wwwdotallelefrequenciesdotnet/defaultdotasp; Gonzalez-Galarza, F F et al., *Nucleic Acid Research* 2015, 28, D784-8).

In choosing an iPSC line from the library one can also consider that recipients can often tolerate maternal non-inherited HLA antigens. Thus, if the prospective recipient's mother's tissue type is known it can be combined with the prospective recipient's tissue type in evaluating potential matches to cell lines in the iPSC library.

In assembling a library of HLA homozygous iPSC lines, the base consideration is the availability of source material. One may work with what nature and happenstance provide or one may make a concerted effort to seek out donors and populations likely to have desired homozygous haplotypes. Yet just because a homozygous cell is available, does not necessarily make it appropriate for inclusion in a particular library. One should consider how common or rare the haplotype is, and how common or rare the individual HLA types or alleles are. One must also consider how the haplotype contributes to the overall coverage of the target population in combination with the haplotypes of the other likely members of the library.

HLA genes are not evenly distributed throughout the human population. Whether one is considering haplotypes or tissue types, their frequency will vary from one target population to another. Thus it is important to consider what target population the HLA homozygous iPSC line library is intended to serve. Populations can be defined in terms of geographic and national borders, by ethnicity, or by a combination thereof. The library can be assembled to maximize coverage of a single target population, or it can be assembled to maximize coverage for multiple distinct populations found within a particular service area. Even if the library is constructed with one particular population in mind, it can be useful to evaluate how well if covers other populations the library's service area. There will also be individuals who [are simply lucky and] will be able to find a compatible match despite not being part of the target population.

In evaluating HLA frequencies of the United States population, it has become standard practice to stratify the population into for ethnic divisions: Caucasian, African-American, Hispanic, and Asian or Pacific Islander. HLA frequency data at the level of either genotype or serotype for individual loci and for haplotypes is readily available on the internet, for example, at the web site of the National Marrow Donor Program (NMDP) (bioinformaticsdotbethematchclinicaldotorg). From a global perspective, HLA frequency data is typically aggregated by geographic regions: North America; South and Central America, and Caribbean; Europe; North Africa; sub-Saharan Africa; Western Asia; Central Asia; North-East Asia; South Asia; South-East Asia; Australia; and Oceania (see the Allele Frequency Net Database, referenced above). However, the actual data is collected from a variety of studies of local national and ethnic populations and medical databases, so it is possible to compile frequencies of more narrowly defined populations as well (see for example Eupedia's *Distribution of HLA-A alleles by country*; wwwdoteupediadotcom/genetics/HLA-A_allele_frequencies_by_countrydotshtml).

Haplotype frequencies for various US sub-populations are available from the NMDP (bioinformaticsdotbethematchclinicaldotorg). They have catalogued 26,447 three-locus haplotypes, for HLA-A and HLA-B (class I) at antigen-level resolution and HLA-DRB1 (class II) at allele-level resolution, across the four commonly used ethnic denominations: Caucasian, African-American, Hispanic, and Asian or Pacific Islander. The use of antigen-level resolution typing for the class I loci and allele-level resolution typing for the class II locus reflects, in part, the more extensive data and understanding of the serologic typing of the class I loci as compared to the class II loci. Extensive typing of the class II loci is more recent and has relied on DNA typing to a greater extent. Thus the correlation between serologic type and gene sequence is more robust for the class I loci and assignment to a serologic type from sequence data alone can be made with greater confidence than for the class II loci. It should be understood that different data sets based on different sets of donors and/or different typing methods (e.g., antigen-level vs. allele-level typing, etc.) will lead to different observations haplotype frequency within the same defined population. Such differences do not indicate that one or the other data set is wrong, but reflect only experimental variation and the fact that all such measures are approximations. As a general rule, the larger the sample size the more reliable and precise the frequencies will be.

The Caucasian subpopulation is the largest of these four subdivisions, constituting a majority of the US population, but is the least diverse genetically. More than 12,500 haplotypes with a frequency of at least $1 \times 10^{-6}$ per diploid genome have been observed. Eight haplotypes had a frequency >1%, three had a frequency over 2%, and the most common haplotype had a frequency >6%. Table 3 presents the 30 most common haplotypes observed in the Caucasian population in the NMDP data set, and their frequencies. For the Caucasian population, 25.5% and 29.7% of individuals would be predicted to have a matching haplotype in a library representing the 20 or 30 most common haplotypes, respectively, evaluated at this level of resolution.

TABLE 3

Top 30 NMDP Caucasian Haplotypes

| | Haplotype | | | |
|---|---|---|---|---|
| Rank | A | B | DRB1 | Frequency |
| 1 | 1 | 8 | 0301 | 0.062183 |
| 2 | 3 | 7 | 1501 | 0.030198 |
| 3 | 2 | 44 | 0401 | 0.020677 |
| 4 | 2 | 7 | 1501 | 0.019904 |
| 5 | 29 | 44 | 0701 | 0.015507 |
| 6 | 2 | 62 | 0401 | 0.012410 |
| 7 | 1 | 57 | 0701 | 0.011211 |
| 8 | 3 | 35 | 0101 | 0.011204 |
| 9 | 2 | 8 | 0301 | 0.008890 |
| 10 | 2 | 60 | 1302 | 0.008143 |
| 11 | 24 | 7 | 1501 | 0.007100 |
| 12 | 2 | 57 | 0701 | 0.006801 |
| 13 | 2 | 44 | 0701 | 0.006729 |
| 14 | 30 | 13 | 0701 | 0.006485 |
| 15 | 23 | 44 | 0701 | 0.006034 |
| 16 | 2 | 13 | 0701 | 0.005505 |
| 17 | 26 | 38 | 0402 | 0.005399 |
| 18 | 11 | 35 | 0101 | 0.005344 |
| 19 | 1 | 7 | 1501 | 0.005224 |
| 20 | 25 | 18 | 1501 | 0.004997 |
| 21 | 2 | 62 | 1301 | 0.004926 |
| 22 | 2 | 44 | 1501 | 0.004854 |
| 23 | 33 | 14 | 0102 | 0.004814 |
| 24 | 2 | 44 | 1301 | 0.004738 |
| 25 | 24 | 35 | 1104 | 0.004679 |
| 26 | 31 | 60 | 0404 | 0.004561 |
| 27 | 2 | 44 | 0101 | 0.004136 |
| 28 | 2 | 50 | 0701 | 0.004052 |
| 29 | 1 | 8 | 1501 | 0.003846 |
| 30 | 2 | 27 | 0101 | 0.003831 |

The Hispanic subpopulation is the second largest of these four subdivisions. The NMDP observed more than 13,500 haplotypes with a frequency of at least $1 \times 10^{-6}$ per diploid genome. Four haplotypes had a frequency >1%, but none over 2%. Table 4 presents the 30 most common haplotypes observed in the Hispanic population in the NMDP data set, and their frequencies. For the Hispanic population, 15.6% and 19.4% of individuals would be predicted to have a matching haplotype in a library representing the 20 or 30 most common haplotypes, respectively, evaluated at this level of resolution.

TABLE 4

Top 30 NMDP Hispanic Haplotypes

| Rank | Haplotype A | B | DRB1 | Frequency |
|---|---|---|---|---|
| 1 | 29 | 44 | 0701 | 0.018354 |
| 2 | 1 | 8 | 0301 | 0.016801 |
| 3 | 2 | 35 | 0802 | 0.015645 |
| 4 | 3 | 7 | 1501 | 0.011575 |
| 5 | 68 | 39 | 0407 | 0.008870 |
| 6 | 2 | 39 | 0407 | 0.007890 |
| 7 | 33 | 14 | 0102 | 0.007751 |
| 8 | 24 | 39 | 1406 | 0.007170 |
| 9 | 30 | 18 | 0301 | 0.006947 |
| 10 | 2 | 35 | 0407 | 0.006589 |
| 11 | 2 | 7 | 1501 | 0.005933 |
| 12 | 24 | 35 | 1104 | 0.005622 |
| 13 | 2 | 44 | 0701 | 0.005621 |
| 14 | 2 | 62 | 0802 | 0.004986 |
| 15 | 23 | 44 | 0701 | 0.004610 |
| 16 | 31 | 35 | 0802 | 0.004578 |
| 17 | 2 | 44 | 1301 | 0.004458 |
| 18 | 24 | 35 | 0407 | 0.004397 |
| 19 | 24 | 61 | 0802 | 0.004371 |
| 20 | 1 | 57 | 0701 | 0.004279 |
| 21 | 24 | 61 | 0407 | 0.004116 |
| 22 | 2 | 61 | 0802 | 0.003995 |
| 23 | 3 | 35 | 0101 | 0.003954 |
| 24 | 2 | 51 | 0802 | 0.003904 |
| 25 | 30 | 13 | 0701 | 0.003881 |
| 26 | 3 | 51 | 0701 | 0.003753 |
| 27 | 68 | 14 | 0102 | 0.003733 |
| 28 | 2 | 44 | 0401 | 0.003694 |
| 29 | 68 | 48 | 0404 | 0.003567 |
| 30 | 24 | 35 | 0802 | 0.003502 |

The African-American subpopulation is the genetically most diverse of these four subdivisions. The NMDP observed more than 13,500 haplotypes with a frequency of at least $1\times10^{-6}$ per diploid genome. Only two haplotypes had a frequency >1%, and none were over 2%. Table 5 presents the 30 most common haplotypes observed in the African-American population in the NMDP data set, and their frequencies. For the African-American population, 10.3% and 13.2% of individuals would be predicted to have a matching haplotype in a library representing the 20 or 30 most common haplotypes, respectively, evaluated at this level of resolution.

TABLE 5

Top 30 NMDP African-American Haplotypes

| Rank | Haplotype A | B | DRB1 | Frequency |
|---|---|---|---|---|
| 1 | 30 | 42 | 0302 | 0.014263 |
| 2 | 1 | 8 | 0301 | 0.011868 |
| 3 | 33 | 53 | 0804 | 0.007239 |
| 4 | 68 | 58 | 1201 | 0.007201 |
| 5 | 3 | 7 | 1501 | 0.006385 |
| 6 | 36 | 53 | 1101 | 0.006151 |
| 7 | 34 | 44 | 1503 | 0.005485 |
| 8 | 2 | 44 | 0401 | 0.005146 |
| 9 | 30 | 42 | 0804 | 0.004910 |
| 10 | 68 | 70 | 0301 | 0.004877 |
| 11 | 29 | 44 | 0701 | 0.004269 |
| 12 | 2 | 7 | 1501 | 0.003798 |
| 13 | 23 | 70 | 0701 | 0.003615 |
| 14 | 23 | 70 | 1101 | 0.003372 |
| 15 | 30 | 57 | 1301 | 0.003082 |
| 16 | 74 | 70 | 1302 | 0.003059 |
| 17 | 66 | 58 | 1503 | 0.002979 |
| 18 | 30 | 14 | 1503 | 0.002971 |
| 19 | 2 | 53 | 1302 | 0.002783 |
| 20 | 68 | 53 | 1503 | 0.002735 |
| 21 | 2 | 42 | 0302 | 0.002658 |
| 22 | 3 | 35 | 0101 | 0.002654 |
| 23 | 2 | 53 | 0804 | 0.002640 |
| 24 | 68 | 7 | 1503 | 0.002611 |
| 25 | 2 | 45 | 1302 | 0.002600 |
| 26 | 74 | 70 | 1101 | 0.002595 |
| 27 | 33 | 63 | 0102 | 0.002451 |
| 28 | 23 | 7 | 1503 | 0.002433 |
| 29 | 2 | 62 | 0401 | 0.002402 |
| 30 | 1 | 57 | 0701 | 0.002373 |

The Asian and Pacific Islander subpopulation is the smallest and has the geographically most diverse ancestry of these four subdivisions. The NMDP observed more than 11,500 haplotypes with a frequency of at least $1\times10^{-6}$ per diploid genome. Eight haplotypes had a frequency >1%, but none were over 2%. The most common haplotypes observed in this group are largely distinct from those of the other 3 subdivisions which have several higher frequency haplotypes in common. Table 6 presents the 30 most common haplotypes observed in the Asian and Pacific Islander population in the NMDP data set, and their frequencies. For the Asian and Pacific Islander population, 17.8% and 22.0% of individuals would be predicted to have a matching haplotype in a library representing the 20 or 30 most common haplotypes, respectively, evaluated at this level of resolution.

TABLE 6

Top 30 NMDP Asian and Pacific Islander Haplotypes

| Rank | Haplotype A | B | DRB1 | Frequency |
|---|---|---|---|---|
| 1 | 33 | 58 | 0301 | 0.019323 |
| 2 | 33 | 44 | 0701 | 0.016077 |
| 3 | 2 | 46 | 0901 | 0.014848 |
| 4 | 24 | 52 | 1502 | 0.012177 |
| 5 | 33 | 44 | 1302 | 0.011553 |
| 6 | 30 | 13 | 0701 | 0.011410 |
| 7 | 33 | 58 | 1302 | 0.011260 |
| 8 | 1 | 57 | 0701 | 0.010689 |
| 9 | 11 | 75 | 1202 | 0.009466 |
| 10 | 24 | 7 | 0101 | 0.008143 |
| 11 | 24 | 35 | 1202 | 0.007326 |
| 12 | 2 | 46 | 0803 | 0.007228 |
| 13 | 1 | 37 | 1001 | 0.006629 |
| 14 | 11 | 62 | 0406 | 0.006346 |
| 15 | 24 | 54 | 0405 | 0.005637 |
| 16 | 24 | 38 | 1502 | 0.005567 |
| 17 | 29 | 7 | 1001 | 0.005333 |
| 18 | 24 | 75 | 1202 | 0.004551 |
| 19 | 2 | 60 | 0901 | 0.004451 |
| 20 | 26 | 8 | 0301 | 0.004399 |
| 21 | 11 | 13 | 1501 | 0.004397 |
| 22 | 11 | 46 | 0901 | 0.004236 |
| 23 | 2 | 61 | 1501 | 0.004028 |
| 24 | 2 | 13 | 1202 | 0.003921 |
| 25 | 24 | 60 | 0901 | 0.003744 |
| 26 | 24 | 61 | 0901 | 0.003527 |
| 27 | 2 | 61 | 0901 | 0.003506 |
| 28 | 11 | 38 | 1502 | 0.003317 |
| 29 | 11 | 62 | 1202 | 0.003293 |
| 30 | 2 | 75 | 1202 | 0.003245 |

While increasing the above haplotype sets from the 20 to the 30 most common haplotypes in each population did increase the proportion of the prospective target populations that would have a matching haplotype, the rate of increase declines after 10-20 of the top ranking haplotypes have been included (see FIG. 1). The rate of increase in the percentage of the indicated populations having at least one matching haplotype as more haplotypes are added to the set is smallest for the African-American population due to its greater genetic diversity. Conversely, the Caucasian population shows the greatest rate of increase due to its comparatively restricted genetic diversity. Even with a library of 100 iPSC lines harboring the 100 most common haplotypes, a Caucasian library would still provide haplotype matches for less than 45% of the corresponding prospective recipient population and an African-American library for just over 25% (see FIG. 1). Actual coverage to the populations would be somewhat better due to matching tissue types arising from complementary, non-matching haplotypes, but that contribution is relatively modest (see Example 6). In addition to being uncommon, such matches will generally be less satisfactory as well as there are likely to be mismatches at non-evaluated loci in the MHC while with a true haplotype match the non-evaluated loci are also likely to match.

The United States population poses a particular challenge in assembling iPSC line libraries that cover a substantial portion of the country's population due to the degree of genetic diversity even within the four subpopulations that the NMDP data is stratified into, and the limited correlation of ethnic/genetic background with geographic location within the country. For countries or regions where there is a high correlation between ethnic/genetic background and geographic location (for example, Japan, Korea, the nations of Europe, those regions of China where the population is predominantly Han Chinese, etc.) it is more feasible to assemble a library of limited size that will cover a substantial portion of a geographically- or nationality-defined population. It can be advantageous to assemble multiple ethnically-focused libraries of moderate size—and without regard for geographic location—rather than larger, more universal libraries. To some extent this is an issue of distribution. For a single institution there may be little difference between assembling several smaller libraries or one large library. Even if there is in effect a single, large library, ethnically-defined sub-libraries could be distributed to other institutions according to the make-up of the population that institution serves. Indeed individual iPSC cell lines could be shipped elsewhere as needed. However, an institution assembling a library primarily for its own use, rather than for broader distribution, can afford to focus on the make-up of the local population that constitutes its principal patient pool.

Figure 2:
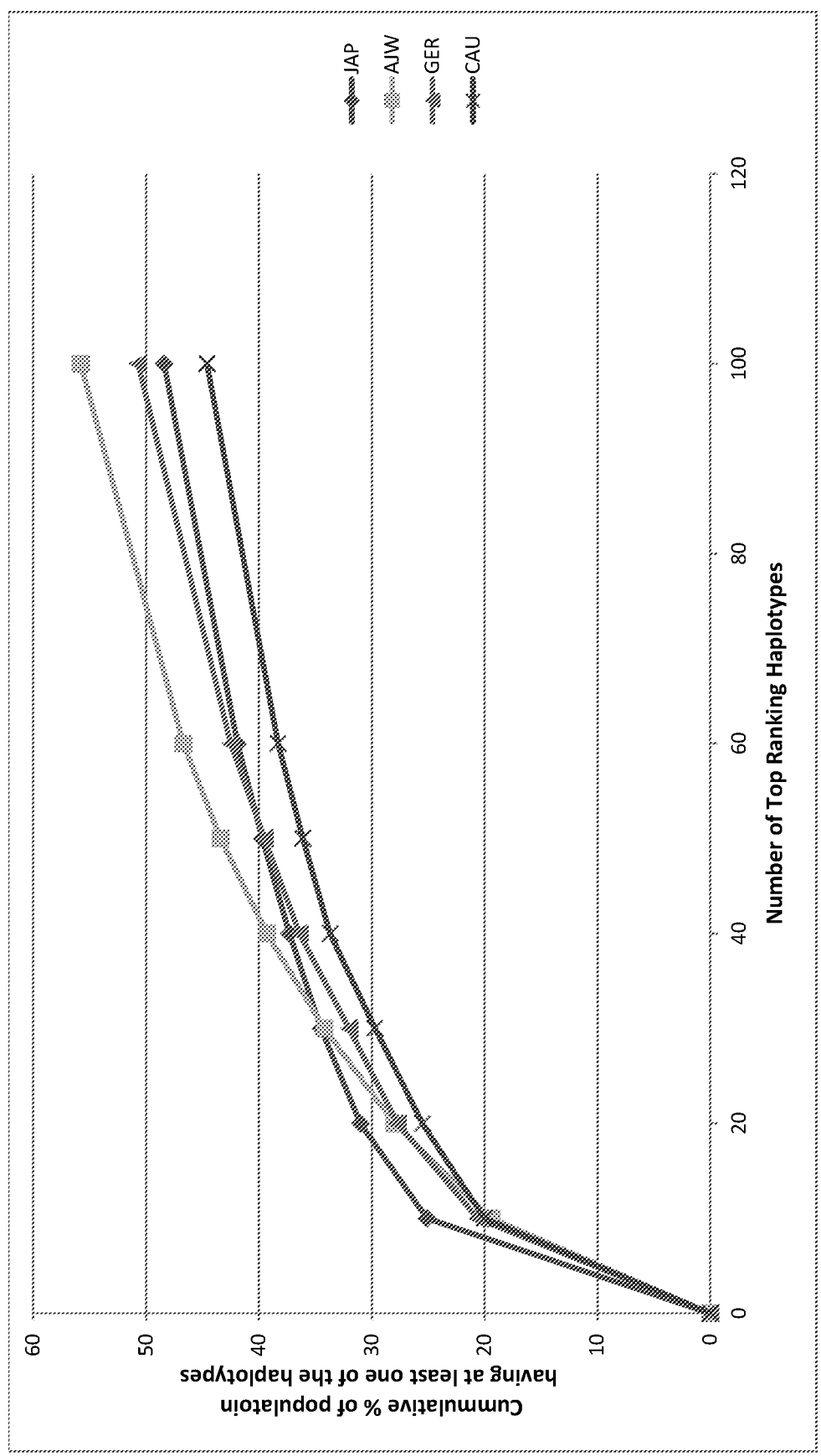
FIG. 2 depicts the cumulative percentage of the population possessing the most frequent haplotypes for three relatively homogenous populations: Japanese living in the same locale as their grandparents; Ashkenazi Jews in an Israeli Bone Marrow Donor Registry; and German blood donors. The data for Caucasians from FIG. 1 is also plotted for comparison.

Again using the Haplotype Frequency Search tool at the at the Allele Frequency Net Database, the cumulative likelihood of matching at least one haplotype in a library of the most common haplotypes for library sizes up to 100 haplotypes was assessed for three relatively homogenous populations: Japanese living in the same locale as their grandparents (Japan pop 16; JAP), Ashkenazi Jews in Israel (Ezer Mizion Bone Marrow Donor Registry; AJW) and German blood donors (Germany pop 7; GER). In general, the cumulative percentage of the population rose more quickly with increasing number of haplotypes, and tended toward leveling off more slowly, than it did for even the NMDP Caucasian subpopulation (see FIG. 2) further illustrating that the less diverse (more homogenous) the target population is, the greater coverage one can get with a given number of appropriately chosen haplotypes.

Cell lines that are homozygous for HLA-A, -B, -DR can be, and are even likely to be, homozygous at additional HLA loci. For example, the DQ locus is adjacent to the DR locus and there is a relatively small region of DNA in which meiotic crossover would have to occur to separate the linked alleles. Similarly, if homozygosity is observed for HLA-A and -B then homozygosity is likely for HLA-C as well. This is because the HLA-C locus is between those of HLA-A and -B. While the distances from the HLA-B locus to the HLA-C locus and from the HLA-C locus to the HLA-A locus are larger than that from the DQ locus to the DR locus, there would need to be two meiotic crossover events, one between the HLA-B locus and the HLA-C locus and one between the HLA-C locus and the HLA-A locus, in order to maintain the linkage between HLA-A and -B while severing the linkage of those two loci to HLA-C.

In embodiments disclosed herein, the homozygous iPSC line library contains 20 cell lines, each harboring a unique haplotype. In other embodiments the library contains 30, 40, 50 . . . 100 cell lines. In still other embodiments the library contains up to 1000 cell lines.

In various embodiments, the library will be expected to provide a match for at least 5, 10, 15, 25, 30, 35, 40, 45, 50, 55, or 60 percent of a target population. Likelihood of matching is evaluated with consideration of HLA-A, -B, and -DRB1. The evaluation may further include any or all of HLA-C, -DP, -DQ, and additional -DR loci. In aspects of these embodiments, the likelihood of providing a match is evaluated at antigen-level resolution for 0 to 6 loci. In further aspects of these embodiments the likelihood of providing a match is evaluated at allele-level resolution for 0 to 6 loci. In some aspects of these embodiments, the evaluation assesses likelihood of a match only considering likelihood of the prospective recipient having the same haplotype as one of the library lines. In other aspects, the evaluation assesses likelihood of a match additionally considering the likelihood of the prospective recipient having complementary, non-matching haplotypes for one of the library lines. In various embodiments, haplotype frequency for the target population is assessed in a data set of at least 2,000 samples, at least 4,000 samples, at least 10,000 samples, at least 15,000, at least 20,000 sample, or at least 25,000 samples.

A single library can be evaluated for coverage of a single target population or multiple target populations. In the former instance, the library can target a single ethnic or geographic population. In the latter instance, the library can target a geographic population comprising multiple distinct ethnic populations.

Target populations can be any ethnic group, any nationality, any geographic region, or the service region of any institution providing stem cell therapies. Without limiting the breadth of the invention and purely by way of example, ethnic groups can include Japanese, Han Chinese, Koreans, Pacific Islanders, Native Americans, African-Americans, Hispanics, Caucasians, Europeans, Northern Europeans, Southern Europeans, Scandinavians, Poles, Slavs, Germans, Italians, French, Russians, Ashkenazi Jews, Mizrahi Jews, Arabs, Persians, etc. Without limiting the breadth of the invention, and purely by way of example, regions can include North America; South and Central America, and Caribbean; Europe; North Africa; sub-Saharan Africa; Western Asia; Central Asia; North-East Asia; South Asia; South-East Asia; Australia; and Oceania; either as commonly used or as defined by the Allele Frequency Net Database. Similarly, the term "region" can refer to a metropolitan area (for example, Greater New York City), a portion of a country or other politically defined entity (for example, the Midwestern US), or a geographic area (for example, the Mediterranean basin, Southeast Asia, or the Middle East).

In assembling a library, one can proceed only as homozygous cells become available. The likelihood of encountering a homozygous donor will reflect the frequency of the haplotype in the donor population. Thus, the use of homozygous donors biases in favor of high frequency haplotypes. Nonetheless it can be appropriate to consider whether any particular homozygous haplotype is a desirable addition to any particular library being assembled in light of the target population for which it is being assembled and the total number of cell lines the completed library is to contain. In many cases the donor and prospective recipient populations will be the same, but not necessarily. The population frequency of HLA haplotypes rapidly drop from the most frequent, thus becoming increasingly less likely to be encountered and decreasingly important for enhancement of the iPSC array's effective population coverage. This is true with every ethnic group and makes finding the next most frequent HLA homozygote progressively more difficult and its expected contribution to the overall usefulness of the Array, smaller. Thus, adding HLA homozygous iPSC lines to the array must be a process mindful of each haplotype's frequency and of the effect of its addition on the cost-benefit ratio. It is entirely acceptable, and potentially preferable, for an iPSC library to not contain all of the 10, 20, 30, 40, 50, or more, most common haplotypes in the population to be served. As an array to serve a target population is assembled or expanded, availability of an iPSC line will often be more important than the absolute rank of its haplotype in the target population. Thus it will often make sense to include an iPSC line that is relatively common in one population in arrays intended to serve other populations, in which the haplotype is substantially less common, due to its availability for inclusion and its relatively modest difference in frequency as compared to higher ranked haplotypes that are outside the most common haplotypes, for example the top 5 to 20 ranked haplotypes, for the targeted population. Especially once a basic iPSC line library is established, rather than expanding the array as more homozygous cells are obtained, the homozygous cells can be stored frozen and only reprogrammed into iPSCs upon need for that haplotype.

The donor population and the service population will often be the same, but they need not be. In fact it can be advantageous to focus donor screening efforts on more genetically homogenous subpopulations where homozygosity is more likely to be encountered. While the ranking of allele frequencies may not reflect that of a broad or mixed service population, haplotypes that are very common in one subpopulation can be expected to be present at a useful frequency among humans in general.

Example 1 discloses a panel of 20 homozygous haplotypes that can be used to constitute an iPSC library targeting the US population generally. One of the haplotypes, A1, B8, DRB1*03:01, was the most common in the Caucasian (CAU) subpopulation and the 2nd most common in the Hispanic (HIS) and African-American (AFA) subpopulations, but rank only 36th in the Asian and Pacific Islander (API) subpopulation (see Table 7). This homozygous haplotype would certainly be desirable to include in any library targeted to the US population or the CAU, HIS, or AFA subpopulations, but would be a more marginal choice for a library specifically targeting the API subpopulation if the library was going to be limited to only 20-25 iPSC lines. However, as explained above if, for example, a haplotype ranked 15-25 were not available, this haplotype could be included with minimal impact on the overall coverage of the API population despite ranking only 36th. If the API-targeted library was going to contain 40 or more lines, then this haplotype would be desirable to include. It would also be a good haplotype to include in any library targeting various Irish, English, Polish, German, Scandinavian, Italian, Spanish, Portuguese, and North African Jewish populations.

The same panel also contains the haplotype A33, B58, DRB1*03:01. This was the most commonly observed haplotype in the API subpopulation and clearly would be appropriate to include in library of any size targeting the API subpopulation individually or as part of a more general population. However, for the CAU, HIS, and AFA subpopulations this same haplotype ranked only 668th, 1003rd, and 471st, respectively. Thus, it would only become desirable to include this haplotype in a library specifically targeting these subpopulations, individually or as a group, if the library were to contain several hundred cell lines.

In preferred embodiments the library will contain all haplotypes occurring at a frequency of >2%, >3% or >4% in the targeted population of prospective recipients. In preferred embodiments the library will contain ≥50%, ≥60%, ≥70%, ≥80%, ≥90%, or all haplotypes occurring at a frequency of >1% in the targeted population of prospective recipients. In various aspects of these embodiments frequency shall be evaluated based on a data set for the targeted population containing at least 2000 samples, at least 4000 samples, at least 10,000 samples, at least 15,000, at least 20,000 sample, or at least 25,000 samples.

In some embodiments, a library of 30 iPSC lines will contain haplotypes providing a match for at least 20%, 25%, 30%, 35%, or 40% of the targeted population.

In some embodiments, an iPSC library with contain the five most common haplotypes for the targeted population. In some embodiments, an iPSC library with contain at least 10 of the 20 to 30 most common haplotypes for the targeted population with each included integer and sub-range constituting a distinct embodiment. In some embodiments an iPSC library will contain at least 10 to at least 20 of the 30 most common haplotypes for the targeted population, with each included integer and sub-range constituting a distinct embodiment. In some embodiments, an iPSC library will contain at least one third to at least two thirds of the most common haplotypes within the total number of iPSC lines in the library, with individual fraction or sub-range constituting a distinct embodiment. Thus an iPSC line library containing 100 HLA homozygous cell lines would include at least 34 to at least 67 of the 100 most common haplotypes in the targeted population, with each included integer and sub-range constituting a distinct embodiment. In further aspects of these embodiments, the library will include the 3, 4, 5, 6, 7, or 8 most common haplotypes in the targeted population.

In further embodiments a library may be constructed as a hybrid of the single subpopulation focused libraries described above. For example, a library containing the 5 most frequent haplotypes in each of the CAU, HIS, and AFA—or CAU, HIS, AFA, and API—subpopulations could be assembled. Other defined subpopulations could be used instead in any number desired. Similarly, instead of the 5 most common haplotypes it could be, for example, 4 of the 8 most common. Finally, the more populous or more genetically diverse subpopulation(s) of the group can be over-represented. For example, a library could comprise 7 of the 10 highest frequency haplotypes from the CAU subpopulation, 6 of the 10 highest frequency haplotypes from the HIS subpopulation, 4 of the 10 highest frequency haplotypes from the AFA subpopulation, and the 3 most common haplotypes in the API subpopulation. The foregoing are only examples and other libraries can be assembled according to the principles exemplified.

The following tables 7-10 provide the 40 most common haplotypes based on high resolution typing for HLA-A, -B, and -DRB1 in four US sub-populations: European Caucasian (EUR), African-America (AFA); Hispanic (HIS); and Asian &Pacific Islander (API). The allele designations in this table with the "g" suffix refer to allele groups defined in Table 2 (Maiers, M., Gragert, L., Klitz, W. High resolution HLA alleles and haplotypes in the US population. 2007).

TABLE 7

| EUR_rank | A | B | DRB1 | EUR_freq |
|---|---|---|---|---|
| 1 | 0101g | 0801g | 0301 | 0.07404 |
| 2 | 0301g | 0702g | 1501 | 0.03524 |
| 3 | 0201g | 4402g | 0401 | 0.02561 |
| 4 | 0201g | 0702g | 1501 | 0.02321 |
| 5 | 2902 | 4403 | 0701 | 0.01859 |
| 6 | 0201g | 1501g | 0401 | 0.01687 |
| 7 | 0101g | 5701 | 0701 | 0.01371 |
| 8 | 0301g | 3501g | 0101 | 0.01275 |
| 9 | 0201g | 4001g | 1302 | 0.00970 |
| 10 | 3001 | 1302 | 0701 | 0.00954 |
| 11 | 0201g | 0801g | 0301 | 0.00896 |
| 12 | 0201g | 5701 | 0701 | 0.00881 |
| 13 | 2402g | 0702g | 1501 | 0.00821 |
| 14 | 1101g | 3501g | 0101 | 0.00738 |
| 15 | 3301 | 1402 | 0102 | 0.00730 |
| 16 | 2301g | 4403 | 0701 | 0.00697 |
| 17 | 0101g | 0702g | 1501 | 0.00675 |
| 18 | 0201g | 1501g | 1301 | 0.00674 |
| 19 | 0201g | 1302 | 0701 | 0.00631 |
| 20 | 3101 | 4001g | 0404 | 0.00613 |
| 21 | 2501 | 1801g | 1501 | 0.00589 |
| 22 | 0201g | 4403 | 0701 | 0.00585 |
| 23 | 0201g | 4402g | 1301 | 0.00565 |
| 24 | 0201g | 4402g | 0101 | 0.00530 |
| 25 | 0101g | 0801g | 1501 | 0.00515 |
| 26 | 0301g | 0702g | 0101 | 0.00508 |
| 27 | 0201g | 4402g | 1501 | 0.00503 |
| 28 | 0201g | 5101g | 1101 | 0.00488 |
| 29 | 2601g | 3801 | 0402 | 0.00473 |
| 30 | 0201g | 2705g | 0101 | 0.00462 |
| 31 | 0301g | 0801g | 0301 | 0.00444 |
| 32 | 3002 | 1801g | 0301 | 0.00436 |
| 33 | 0201g | 1801g | 1104 | 0.00425 |
| 34 | 2402g | 0801g | 0301 | 0.00425 |
| 35 | 2402g | 3502 | 1104 | 0.00416 |
| 36 | 0201g | 1501g | 0101 | 0.00365 |
| 37 | 1101g | 0702g | 1501 | 0.00361 |
| 38 | 6802 | 1402 | 1303 | 0.00343 |
| 39 | 0201g | 5101g | 1301 | 0.00343 |
| 40 | 0201g | 1501g | 1501 | 0.00341 |

TABLE 8

| AFA_rank | A | B | DRB1 | AFA_freq |
|---|---|---|---|---|
| 1 | 3001 | 4201 | 0302 | 0.01542 |
| 2 | 0101g | 0801g | 0301 | 0.01169 |
| 3 | 6801g | 5802 | 1201g | 0.00782 |
| 4 | 6802 | 1510 | 0301 | 0.00713 |
| 5 | 3303 | 5301 | 0804 | 0.00697 |
| 6 | 3601 | 5301 | 1101 | 0.00676 |
| 7 | 0301g | 0702g | 1501 | 0.00673 |
| 8 | 3402 | 4403 | 1503 | 0.00623 |
| 9 | 2902 | 4403 | 0701 | 0.00586 |
| 10 | 0201g | 4402g | 0401 | 0.00539 |
| 11 | 2301g | 1503g | 0701 | 0.00501 |
| 12 | 7401g | 1503g | 1302 | 0.00490 |
| 13 | 6802 | 0702g | 1503 | 0.00391 |
| 14 | 3001 | 4201 | 0804 | 0.00384 |
| 15 | 3002 | 1402 | 1503 | 0.00375 |

TABLE 8-continued

| AFA_rank | A | B | DRB1 | AFA_freq |
|---|---|---|---|---|
| 16 | 6802 | 5301 | 1503 | 0.00364 |
| 17 | 7401g | 5703 | 1303 | 0.00356 |
| 18 | 2902 | 4901 | 1503 | 0.00351 |
| 19 | 2301g | 4403 | 1503 | 0.00337 |
| 20 | 0201g | 0801g | 0301 | 0.00300 |
| 21 | 0201g | 1501g | 0401 | 0.00297 |
| 22 | 6602 | 5801g | 1503 | 0.00293 |
| 23 | 0201g | 4501g | 1302 | 0.00289 |
| 24 | 6601 | 5802 | 1301 | 0.00287 |
| 25 | 2301g | 1503g | 1503 | 0.00287 |
| 26 | 0201g | 0702g | 1101 | 0.00282 |
| 27 | 2301g | 5301 | 1101 | 0.00274 |
| 28 | 0201g | 4501g | 1503 | 0.00272 |
| 29 | 6802 | 5301 | 1303 | 0.00267 |
| 30 | 7401g | 1503g | 1503 | 0.00264 |
| 31 | 2301g | 5301 | 0701 | 0.00250 |
| 32 | 2301g | 0702g | 0901 | 0.00246 |
| 33 | 0201g | 5101g | 1303 | 0.00245 |
| 34 | 2301g | 4201 | 0302 | 0.00240 |
| 35 | 6802 | 5301 | 1302 | 0.00235 |
| 36 | 0301g | 5802 | 0701 | 0.00234 |
| 37 | 2301g | 4403 | 0701 | 0.00232 |
| 38 | 2501 | 1801g | 1501 | 0.00230 |
| 39 | 2601g | 0801g | 1304 | 0.00227 |
| 40 | 6802 | 4201 | 0302 | 0.00227 |

TABLE 9

| HIS_rank | A | B | DRB1 | HIS_freq |
|---|---|---|---|---|
| 1 | 2902 | 4403 | 0701 | 0.01702 |
| 2 | 0101g | 0801g | 0301 | 0.01538 |
| 3 | 0301g | 0702g | 1501 | 0.01293 |
| 4 | 3002 | 1801g | 0301 | 0.00823 |
| 5 | 3301 | 1402 | 0102 | 0.00788 |
| 6 | 6803 | 3905 | 0407 | 0.00652 |
| 7 | 2301g | 4403 | 0701 | 0.00636 |
| 8 | 2402g | 3906 | 1406 | 0.00595 |
| 9 | 0201g | 0702g | 1501 | 0.00587 |
| 10 | 0206 | 3905 | 0407 | 0.00552 |
| 11 | 0201g | 3517 | 0802 | 0.00545 |
| 12 | 2402g | 3502 | 1104 | 0.00504 |
| 13 | 0201g | 3512 | 0802 | 0.00448 |
| 14 | 0201g | 1515 | 0802 | 0.00445 |
| 15 | 0201g | 4402g | 1301 | 0.00439 |
| 16 | 3001 | 1302 | 0701 | 0.00428 |
| 17 | 6802 | 1402 | 0102 | 0.00427 |
| 18 | 0201g | 0801g | 0301 | 0.00417 |
| 19 | 0201g | 4403 | 0701 | 0.00411 |
| 20 | 1101g | 2705g | 0101 | 0.00400 |
| 21 | 6801g | 4801g | 0404 | 0.00390 |
| 22 | 0101g | 5701 | 0701 | 0.00381 |
| 23 | 0301g | 3501g | 0101 | 0.00369 |
| 24 | 0301g | 5101g | 0701 | 0.00365 |
| 25 | 0206 | 4002g | 0802 | 0.00362 |
| 26 | 0201g | 3501g | 0407 | 0.00359 |
| 27 | 0201g | 5101g | 1101 | 0.00358 |
| 28 | 0101g | 0702g | 1501 | 0.00356 |
| 29 | 2402g | 4002g | 0802 | 0.00350 |
| 30 | 0201g | 1402 | 0102 | 0.00347 |
| 31 | 0201g | 3512 | 0407 | 0.00344 |
| 32 | 3101 | 3501g | 0802 | 0.00344 |
| 33 | 2402g | 4002g | 0404 | 0.00334 |
| 34 | 2501 | 1801g | 1501 | 0.00328 |
| 35 | 6801g | 4002g | 0407 | 0.00325 |
| 36 | 2402g | 3905 | 0407 | 0.00319 |
| 37 | 1101g | 5201g | 1502 | 0.00310 |
| 38 | 2601g | 3801 | 0402 | 0.00302 |
| 39 | 0201g | 1501g | 0401 | 0.00302 |
| 40 | 0201g | 1801g | 0301 | 0.00300 |

TABLE 10

| API_rank | A | B | DRB1 | API_freq |
|---|---|---|---|---|
| 1 | 3303 | 5801g | 0301 | 0.02335 |
| 2 | 0207g | 4601 | 0901 | 0.01597 |
| 3 | 3303 | 4403 | 0701 | 0.01499 |
| 4 | 3001 | 1302 | 0701 | 0.01466 |
| 5 | 3303 | 5801g | 1302 | 0.01434 |
| 6 | 1101g | 1502 | 1202 | 0.01216 |
| 7 | 2402g | 5201g | 1502 | 0.01022 |
| 8 | 0101g | 5701 | 0701 | 0.01002 |
| 9 | 3303 | 4403 | 1302 | 0.00866 |
| 10 | 0101g | 3701 | 1001 | 0.00792 |
| 11 | 2901g | 0705g | 1001 | 0.00683 |
| 12 | 2402g | 4001g | 0901 | 0.00607 |
| 13 | 1101g | 4601 | 0901 | 0.00557 |
| 14 | 2402g | 5401 | 0405 | 0.00552 |
| 15 | 2402g | 0702g | 0101 | 0.00550 |
| 16 | 1101g | 4001g | 0803 | 0.00514 |
| 17 | 2601g | 0801g | 0301 | 0.00512 |
| 18 | 1101g | 3802 | 1502 | 0.00508 |
| 19 | 0207g | 4601 | 0803 | 0.00504 |
| 20 | 1101g | 1301 | 1501 | 0.00489 |
| 21 | 1101g | 5401 | 0405 | 0.00488 |
| 22 | 0201g | 1301 | 1202 | 0.00481 |
| 23 | 1101g | 1501g | 0406 | 0.00432 |
| 24 | 2402g | 4001g | 1501 | 0.00417 |
| 25 | 2407 | 3505 | 1202 | 0.00415 |
| 26 | 2402g | 4601 | 0901 | 0.00411 |
| 27 | 2402g | 5101g | 0901 | 0.00410 |
| 28 | 1101g | 4001g | 0901 | 0.00404 |
| 29 | 0201g | 4001g | 1101 | 0.00402 |
| 30 | 0203 | 3802 | 1602 | 0.00360 |
| 31 | 2402g | 4001g | 0403 | 0.00359 |
| 32 | 1101g | 3501g | 1501 | 0.00348 |
| 33 | 2417 | 1502 | 1202 | 0.00341 |
| 34 | 1101g | 4001g | 1501 | 0.00339 |
| 35 | 2402g | 1301 | 1501 | 0.00335 |
| 36 | 1101g | 3901g | 0803 | 0.00334 |
| 37 | 2402g | 5901 | 0405 | 0.00332 |
| 38 | 1101g | 5201g | 1502 | 0.00325 |
| 39 | 0201g | 5101g | 0901 | 0.00323 |
| 40 | 0101g | 0801g | 0301 | 0.00313 |

Further disclosed herein are induced pluripotent stem cells (iPSCs) formed from the identified HLA homozygous cells. The iPSCs can be produced by any cell or tissue including, but not limited to, umbilical cord blood, peripheral blood, bone marrow, adipose tissue, gonadal tissue, and others.

Stem cells are characterized by two distinct capabilities: self-renewal through mitotic cell division and the potential for differentiation into functional cells, tissues and organ. Thus, a critical quality of "sternness" is the unique ability to engage in "asymmetrical division" i.e., to divide producing two different cells: one, a stem cell identical to its parent and the second, a cell with the capacity to engage in differentiation. There is a hierarchy of "sternness", defined by the degree of limitation to the stem cell's capacity to generate any type of cells. Thus, those emerging from the oocyte's first few divisions are totipotential stem cells, able to differentiate into any cell and tissue in the body—plus the extraembryonic, or placental, cells. Pluripotential stem cells, capable of forming the different tissues of the embryo's three germ layers (endo-, meso- and ecto-dermal), but not extraembryonic cells, and multipotential or progenitor stem cells which give rise to only some cell linages, such as the hematopoietic stem cells (HSCs) that originate the various cell types of the blood and immune systems. Pluripotentiality is associated with the expression of functional "molecular markers", such as, but not limited to 5T4, ABCG2, Activin RIB/ALK-4, Alkaline Phosphatase/ALPL, E-Cadherin, Cbx2, CD9, CD30/TNFRSF8, CD117/c-kit, CDX2; CHD1, Cripto, DNMT3B, DPPA2, EpCAM/ TROP1, ERR beta/NR3B2, ESGP, F-box protein 15/FBXO15, FGF-4; FGF-5; FoxD3, GBX2, GCNF/ NR6A1, GDF-3, Integrin alpha 6/CD49f, Integrin beta 1/CD29, KLF4, KLF5, L1TD1, Lefty, LIN-28A, LIN-28B, LIN-41, c-Maf, c-Myc, Nanog, Oct3/4, Oct-4A, Oct-4B, Podocalyxin, Rex-1/ZFP42, Smad2, Smad2/3, SOX2, SSEA-1, STAT3, TBX2, TEX19, TRA-1-60(R), TROP-2, UTF1.

Pluripotent stem cell lines can be derived from embryonic murine (mESC) and human cells (hESC) cultured in-vitro, and have been extensively studied, despite the inherent ethical issues regarding the possible clinical use of the latter, to generate differentiated tissues and cells. Differentiated human adult cells can be induced to become iPSC through the introduction of four transcription factors, Oct4 (Octamer binding transcription factor-4), Klf4 (Kruppel-like factor-4), Sox2 (Sex determining region Y)-box 2, and c-Myc (avian myelocytomatosis viral oncogene [v-Myc] homolog). Although this combination of four factors has been the most frequently reported for the production of iPSC, each of the factors can be functionally replaced by related transcription factors, miRNAs, small molecules and non-related genes such as lineage specifiers, and some even omitted—especially through changes in the p53 gene—in some cases.

In one aspect, a method for preparing an iPSC is provided. The method includes transfecting a cord blood stem cell with nucleic acids encoding an Oct-4 protein, a Sox2 protein, a Klf protein, and a cMyc protein to form a transfected cord blood stem cell. The transfected cord blood stem cell is allowed to divide thereby forming the iPSC line. Other methods of producing iPSC lines are within the scope of the present disclosure.

A "cord blood hematopoietic stem cell" refers to an adult stem cell that resides in cord blood and is characterized by a lesser potency to self renew and differentiate than a pluripotent stem cell. Most hematopoietic stem cells express the CD34+ marker, including cord blood hematopoietic stem cells.

A "cell culture" is a population of cells residing outside of an organism. These cells are optionally primary cells isolated from a cell bank, animal, or blood bank, or secondary cells that are derived from one of these sources and have been immortalized for long-lived in vitro cultures.

The term "transfection" or "transfecting" is defined as a process of introducing nucleic acid molecules to a cell by non-viral or viral-based methods. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection, and electroporation. In some embodiments, the nucleic acid molecules are introduced into a cell using electroporation following standard procedures well known in the art. In some embodiments, the non-viral vector is an episomal vector or a modified RNA. For viral-based methods of transfection any useful viral vector may be used in the methods described herein. Examples for viral vectors include, but are not limited to retroviral, adenoviral, lentiviral, paramyxoviral (including Sendai viral), and adenoassociated viral vectors. In some embodiments, the nucleic acid molecules are introduced into a cell using a paramyxoviral vector following standard procedures well known in the art.

There are multiple methods to generate iPSCs, including virus-mediated gene transduction and chemical induction.

While retroviral vectors require integration into host chromosomes to express reprogramming genes, DNA-based vectors such as adenovirus, adeno-associated virus, and plasmid vectors exist episomally and do not require integration; however, they may still be integrated into host chromosomes at certain frequencies. Unlike these vectors, Sendai virus reprogramming vectors (paramyxoviral vectors) do not integrate into the host genome or alter the genetic information of the host cell. Sendai virus (SeV) is a respiratory virus of mouse and rat, classified as mouse parainfluenza virus type I belonging to the Paramyxoviridae family. SeV is an enveloped virus of 150-250 nm in diameter whose genome is a single chain RNA (15,384 bases) in the minus sense. Six genes coding for viral proteins are situated sequentially on the genome of the wild-type SeV in the following order (starting from the 3' end of the genomic RNA): (1) nucleocapsid protein (NP) which forms the core nucleocapsid complex with the genome RNA; (2) phosphoprotein (P) which is the small subunit of the RNA polymerase; (3) matrix protein (M) which supports the envelope structure from the inside; (4) fusion protein (F) which fuses the viral envelope with cell membrane when the virus enters the cell; (5) hemagglutinin-neuraminidase (HN) which recognizes the cell surface receptor sialic acid; and (6) large protein (L) which is the large subunit of RNA polymerase.

Because SeV infects cells by attaching itself to the sialic acid receptor present on the surface of many different cells, it can infect a wide range of cell types of various animal species. Activation of F protein by a protease is required for the virus-cell fusion process to take place. After infection, the virus goes through genome replication and protein synthesis, and then daughter virus particles are assembled and released. Vectors comprising modified, non-transmissible forms of SeV can safely and effectively deliver and express key genetic factors necessary for reprogramming somatic cells into iPSCs. Deletion of the gene encoding the F protein is renders the vector incapable of producing infectious particles from infected cells. Desirable Sendai vectors are non-integrating and remain in the cytoplasm. In addition, the host cell can be cleared of the vectors and reprogramming factor genes by exploiting the cytoplasmic nature of SeV.

In certain embodiments, the cells are transfected with SeV vector(s) causing the target cells to express all of the transcription factors Oct-4, Sox 2, Klf4, and cMyc. Nucleotide sequences of these factors, within SeV expression vectors, are incorporated into the target cells, causing the cells to express all of the factors. In certain embodiments, the cells are transfected with a fragment comprising less than the full length gene. In such case, the fragment must induce the same activity in the target cell as the full-length gene.

Oct-4 (octamer-binding transcription factor 4) also known as POU5F1 (POU domain, class 5, transcription factor 1) is a protein that in humans is encoded by the POU5F1 gene. Oct-4 is a homeodomain transcription factor of the POU family. This protein is critically involved in the self-renewal of undifferentiated embryonic stem cells. As such, it is frequently used as a marker for undifferentiated cells. Oct-4 has 4 isoforms. The protein sequence (e.g., isoform 1, NCBI NP_002692.2) and nucleotide sequence (e.g., isoform 1, NCBI NM_002701.5) of Oct-4 are publically available.

Sox2 (sex determining region Y)-box 2, is a transcription factor that is essential for maintaining self-renewal, or pluripotency, of undifferentiated embryonic stem cells. A "Sox2 protein" as referred to herein includes any of the naturally-occurring forms of the Sox2 transcription factor, or variants thereof that maintain Sox2 transcription factor activity (e.g. within at least 50%, 80%, 90%, 95%, 96%, 97%, 98%, 99% or 100% activity compared to Sox2). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Sox2 polypeptide. The protein sequence (e.g., NCBI NP_003097.1) and nucleotide sequence (e.g., NCBI NM_003106.3) of Sox2 are publically available.

A "Klf4 protein" as referred to herein includes any of the naturally-occurring forms of the Klf4 transcription factor, or variants thereof that maintain Klf4 transcription factor activity (e.g. within at least 50%, 80%, 90%, 95%, 96%, 97%, 98%, 99% or 100% activity compared to Klf4). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Klf4 polypeptide. The protein sequence (e.g., isoform 1, NCBI NP_001300981.1) and nucleotide sequence (e.g., isoform 1, NCBI NM_001314052.1) of Klf4 are publically available.

A "cMyc protein" as referred to herein includes any of the naturally-occurring forms of the cMyc transcription factor, or variants thereof that maintain cMyc transcription factor activity (e.g. within at least 50%, 80%, 90%, 95%, 96%, 97%, 98%, 99% or 100% activity compared to cMyc). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring cMyc polypeptide. The protein sequence (e.g., NP_002458.2) and nucleotide sequence (e.g., isoform 1, NCBI NM_002467.4) of Klf4 are publically available.

In certain embodiments, the Sendai virus vector is a non-replicative vector. An exemplary Sendai virus vector, while incapable of replication, remains capable of productive expression of nucleic acids encoding protein(s) carried by the vector, thereby preventing any potential uncontrolled spread to other cells or within the body of a subject. This type of Sendai vector is commercially available as a CytoTune™-iPSC Sendai viral vector kit (ThermoFisher Scientific).

Any method suitable to produce stable iPSC with no viral footprint and appropriate preservation of genetic characteristics are appropriate for the reprogramming of HLA homozygous cells for inclusion in the disclosed array or library.

The terms "identical" or percent "identity," in the context of two or more nucleic acids, or one or more polypeptides, refer to two or more sequences or subsequences that are the same or have a specified percentage of residues (nucleotides or amino acids) that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms or by manual alignment and visual inspection (see, e.g., the NCBI web site or the like). Such sequences are then said to be "substantially identical." The definition also includes sequences that have deletions and/or additions, as well as those that have substitutions. The identity exists over a region such as a region that is at least about 25 amino acids or nucleotides in length, over a region that is 50-100 amino acids or nucleotides in length, or a region comprising the entire amino acid or nucleotide sequence as indicated.

Allowing the transfected cord blood stem cell to divide and thereby forming the iPSC may include expansion of the cord blood stem cell after transfection, optional selection for transfected cells and identification of pluripotent stem cells. Expansion, as used herein, includes the production of progeny cells by a transfected cord blood stem cell in containers and under conditions well know in the art. Expansion may occur in the presence of suitable media and cellular growth factors. Cellular growth factors are agents which cause cells to migrate, differentiate, transform or mature and divide. They are polypeptides which can usually be isolated from various normal and malignant mammalian cell types. Some growth factors can also be produced by genetically engineered microorganisms, such as bacteria (E. coli) and yeasts. Cellular growth factors may be supplemented to the media and/or may be provided through co-culture with irradiated embryonic fibroblasts that secrete such cellular growth factors. Examples of cellular growth factors include, but are not limited to FGF, bFGF2, and EGF.

Where appropriate, the expanding transfected cord blood stem cell may be subjected to a process of selection. A process of selection may include a selection marker introduced into a cord blood stem cell upon transfection. A selection marker may be a gene encoding for a polypeptide with enzymatic activity. The enzymatic activity includes, but is not limited to, the activity of an acetyltransferase and a phosphotransferase. In some embodiments, the enzymatic activity of the selection marker is the activity of a phosphotransferase. The enzymatic activity of a selection marker may confer to a transfected cord blood stem cell the ability to expand in the presence of a toxin. Such a toxin typically inhibits cell expansion and/or causes cell death. Examples of such toxins include, but are not limited to, hygromycin, neomycin, puromycin and gentamycin. In some embodiments, the toxin is hygromycin. Through the enzymatic activity of a selection maker a toxin may be converted to a non-toxin, which no longer inhibits expansion and causes cell death of a transfected cord blood stem cell. Upon exposure to a toxin, a cell lacking a selection marker may be eliminated and thereby precluded from expansion.

Identification of the iPSC may include, but is not limited to the evaluation of the afore mentioned pluripotent stem cell characteristics. Such pluripotent stem cell characteristics include without further limitation, the expression or non-expression of certain combinations of molecular markers. Further, cell morphologies associated with pluripotent stem cells are also included in pluripotent stem cell characteristics.

Additional characterizations of the iPSCs can include, but are not limited to, determination of colony and cell morphology in culture including specific immunofluorescence and immunocytochemistry; sterility testing; Mycoplasma testing; presence of endotoxin, determination of residual reprogramming plasmid or factor expression; fow cytometric and immunocytochemistry markers for embryonal germ layer, differentiation, and self-renewal; ability to form embryoid bodies (in vitro) and teratomas; histopathology revealing three-lineage differentiation; expression analysis (cRNA microarrays, Pluritest and hPSC ScoreCard); karyotyping (G-banding); copy number variation (CNV) and comparative genomic hybridization (CGH); characterization of short tandem repeats (STR); and whole genome sequencing. One or more of these characterization assays are performed on the HLA homozygous iPSC lines.

In certain embodiments, the HLA homozygous iPSC are maintained in a cryopreserved library until such time as a need arises for a specific sample for a recipient. At that time the iPSC are thawed, cultured, and differentiated into the cell type needed by the recipient. Once differentiated, the specific cells are then administered to the recipient.

EXAMPLES

The following non-limiting examples are provided for illustrative purposes only in order to facilitate a more complete understanding of representative embodiments now contemplated. These examples should not be construed to limit any of the embodiments described in the present specification.

Example 1

Generation of iPSC from CD34+ Cord Blood Cells

Umbilical cord blood (UCB) is obtained from full-term deliveries after receiving informed consent. UCB is collected in bags containing heparin and processed within 24 hr by cryopreserving. The cord blood is HLA typed and, if homozygous, the cord blood unit is suitable for inclusion in the library and for generation of iPSCs.

After separation over Ficoll Isopaque, low density cells are washed in media supplemented with 2% FCS. CD34+ cells are selected from mononuclear cell suspensions by immunomagnetic cell separation using anti-CD34 antibodies. CD34+ cells are cultured for 5 days in medium supplemented with 10% FBS, human stem cell factor (SCF), human thrombopoietin (TPO), human interleukin-3, rhIL-6, rhIL-6 receptor α, rhFlt3 ligand, human granulocyte macrophage colony-stimulating factor, and rhM-CSF.

Reprogramming of CD34+ UCB cells into iPSCs is performed 5 days after initial culture using SeV vectors encoding Oct-4, Sox2, Klf4, and c-Myc. The floating cells are discarded and the adhesive cells are treated with 0.25% trypsin/EDTA and resuspended in the same medium described above. To transduce cells, SeV vectors containing the four separate reprogramming factors are added to the cell suspension. The four reprogramming factors are included on 1, 2, 3, or 4 different SeV vectors. Vector-transduced cells are immediately plated onto a 12-well plate precoated with 5 μg/cm$^2$ fibronectin (e.g., RetroNectin®, Clontech). The culture plate is centrifuged at 1000×g at 32° C. for 45 min. The next day, medium is replaced with fresh medium. Two days later, cells are trypsinized and passed onto two 10-cm gelatin-coated culture dishes. The cultures are maintained in human embryonic stem cell (hESC) medium containing DMEM/F12, 20% KnockOut® Serum Replacement, 1% minimum essential medium (MEM) nonessential amino acids, 1 mM L-glutamine, 0.1 mM β-mercaptoethanol, and 8 ng/mL of basic fibroblast growth factor (bFGF). iPSC colonies are manually isolated based on morphology between day 14 to day 30 postinfection. iPSC cultures are further maintained on plates coated with MATRIGEL® (BD Biosciences).

Example 2

Teratoma Formation by Human iPSCs iPSC clones generated in Example 1 are tested in a teratoma assay. iPSCs at a concentration of 1×10$^6$/125 μl are injected subcutaneously into the flank of a severe combined immunodeficiency mouse. After 75 days, the mice are euthanized, evaluated for gross evidence of tumor formation, and representative sets of tissues, such as liver, kidneys, spleen, pancreas, adrenal gland, gall bladder, lungs, heart, brain, gastrointestinal tract, urogenital tract, and left hind limb are collected for histology. Collected tissues are fixed in 10% neutral-buffered formalin, paraffin-embedded, routinely processed, and stained with hematoxylin and eosin. A board-certified pathologist evaluates the tissue sections for any evidence of tumor and/or teratoma formation which indicates successful induction of pluripotency.

Example 3

Karyotyping iPSC clones generated in Example 1 are chosen for karyotyping. iPSC cells are plated in a 6-well plate and treated with 20 µl colcemid for 2 hr in a 37° C. incubator to arrest the mitotic cells in metaphase. Colonies are lifted with ACCUTASE® (Stem Cell Technologies) and subsequently centrifuged at 850 rpm for 3 min. The cell pellet is suspended in 0.067 M KCl hypotonic solution and incubated for 20 min at room temperature. A 3:1 methanol:acetic acid fixative solution is added to the hypotonic solution and incubated for 5 min at room temperature. This is followed by 3 rounds of treatment with a 3:1 methanol:acetic acid fixative solution, each round incubated for 1 hr at room temperature. Samples are dropped onto clean wet slides and aged in an oven at 90° F. for 1-2 hr. Afterwards, slides are immersed in trypsin for 30-40 sec and rinsed in fetal bovine serum and saline. After an additional rinse in saline, the slides are stained in 12.5% Giemsa in Gurrs buffer for 2-3 min. Slides are rinsed in distilled water and air dried. Karotype analysis is then conducted on the slides.

Example 4

In Vitro Differentiation of Human iPSCs iPSCs can be differentiated into any type of cell and protocols for such differentiation are known to persons of ordinary skill in the art.

Embryoid bodies are generated from human iPSCs in suspension culture for 6 days in medium with 15% KSR and then grown in adherent culture on gelatin-coated dishes with cytokine cocktails (e.g., 100 ng/ml SCF, 100 ng·ml Flt3L, 50 ng/ml TPO, 100 ng/ml G-CSF, 20 ng/ml IGF-2, and 100 ng/ml VEGF) to induce lymphoid lineage cells and cardiomyocytes.

For differentiation to dopaminergic neurons, iPSCs are cocultured with stromal cells in medium containing 10% KSR, $1\times10^{-4}$ M non-essential amino acids, and 2-mercaptoethanol for 16 days.

For induction of endoderm cells and pancreatic cells, iPSCs are cultured on feeder cells with 100 ng/ml activin A in medium supplemented with 2% FBS for 4 days and followed by an additional 8 days culture in medium supplemented with N2 and B-27 media supplements (both from ThermoFisher Scientific), non-essential amino acids, β-mercaptoethanol, bovine serum albumin, and L-glutamine.

Example 5

Assembly of a Library of iPSC Cell Lines

Cells from twenty cord blood units, each of which has a distinct haplotype that is homozygous at all of HLA-A, -B, and -DRB1 (see Table 11) are treated to induce pluripotency as described above. The cells are propagated to generate a seed stock for each. The seed stock cells are aliquoted and stored frozen in liquid nitrogen ($LN_2$). An aliquot from the seed stock is propagated to generate a working stock which is aliquoted and stored frozen in $LN_2$. An aliquot from the working stock is propagated to generate library stock which is aliquoted and stored frozen in $LN_2$.

Seed stock is used both to generate new working stock when existing working stock becomes depleted and to replenish seed stock. Working stock is used to replenish library stock when it becomes depleted. Quality control assays are conducted on samples from each stock as it is generated to confirm haplotype and insure the lack of contamination with other cell lines, or other organisms including for example, bacteria, yeast, and mold.

TABLE 11

Haplotypes of 20 Cord Blood Units from which an iPSC Line Library is Generated
HLA LOCI

| A | B | DRB1 |
|---|---|---|
| 01:01 | 08:01 | 03:01 |
| 26:01 | 38:01 | 04:02 |
| 03:01 | 07:02 | 15:01 |
| 29:02 | 44:03 | 07:01 |
| 02:01 | 44:02 | 04:01 |
| 02:01 | 35:01 | 04:07 |
| 01:01 | 57:01 | 07:01 |
| 02:06 | 35:12 | 08:02 |
| 02:01 | 07:02 | 15:01 |
| 33:03 | 44:03 | 07:01 |
| 24:02 | 52:01 | 15:02 |
| 01:01 | 35:02 | 11:04 |
| 30:01 | 13:02 | 07:01 |
| 33:03 | 58:01 | 03:01 |
| 02:01 | 39:01 | 04:07 |
| 11:02 | 52:01 | 15:02 |
| 02:01 | 08:01 | 03:01 |
| 33:03 | 53:01 | 08:04 |
| 26:01 | 38:01 | 13:02 |
| 01:01 | 57:01 | 13:05 |

More specifically, quality control assays are used to address five basic issues:

Identity, which must be repeatedly documented, and can be assessed using methods such as STR, SNP and even genomic sequencing.

Genomic Stability, which can be assessed by microarray methods of karyotyping and CNV detection, nanostring technology, and genomic sequencing.

Pluripotency, which can be assessed by marker expression, embryoid body analysis and teratoma formation by immunocytochemistry.

Persistence of expressiong of reprogramming factors, which can be assessed by high sensitivity PCR assays.

Absence of contamination, which can be assessed using standard microbiological assays for bacterial, fungal and mycoplasma in culture.

Example 6

Demographic Comparison of the 20 Haplotypes

Using antigen-level resolution data for HLA-A and -B and allele-level resolution data for DRB1 from the NMDP haplotype frequency and ranking within each of the four demographic groupings is compared. The library contains 9 of the 20 most common haplotypes for the Caucasian (CAU) population, 7 of the 20 most common haplotypes for the Hispanic (HIS) population, 6 of the of the 20 most common haplotypes for the African-American (AFA) population, and 5 of the of the 20 most common haplotypes for the Asian & Pacific Islander (API) population. Thus, the library has iPSC cell lines compatible with a meaningful portion of all four of the defined demographic subpopulations.

alleles the effect may be minimal. Table 12 reports the frequencies of the haplotypes in 2) to 4) generated using the Haplotype Frequency Search function at the Allele Frequency Net Database.

TABLE 13

Frequencies of HLA-A1, B8, DRB1*03:01 related haplotypes

| Haplotype Pattern | HLA-A | HLA-B | HLA-DRB1 | CAU (%) | HIS (%) | AFA (%) | API (%) |
|---|---|---|---|---|---|---|---|
| (1) | 01 | 08 | 03:01 | 6.2 | 1.7 | 1.2 | 0.3 |
| (2) | 01 | 08 | X | 1.4 | 0 | 0 | 0 |
|  | X | X | 03:01 | 2.8 | 1.9 | 1.8 | 2.8 |
| (3) | 01 | X | 03:01 | 0 | 0 | 0 | 0 |
|  | X | 08 | X | 1.9 | 0.6 | 0.6 | 0.6 |
| (4) | 01 | X | X | 11.0 | 1.3 | 0.4 | 2.4 |
|  | X | 08 | 03:01 | 1.9 | 0.6 | 0.3 | 0.6 |

TABLE 12

Haplotypes of 20 Cell Line Library for General Use for the US Population Showing Frequency and Ranking According to the NMDP Data Set

| Haplotype | | | Frequency | | | | Ranking | | | |
|---|---|---|---|---|---|---|---|---|---|---|
| A | B | DRB1 | CAU | HIS | AFA | API | CAU | HIS | AFA | API |
| 1 | 8 | 0301 | 0.062183 | 0.016801 | 0.011868 | 0.002979 | 1 | 2 | 2 | 36 |
| 1 | 35 | 1104 | 0.002630 | 0.002399 | 0.000173 | 0.000640 | 40 | 55 | 1206 | 298 |
| 1 | 57 | 0701 | 0.011211 | 0.004279 | 0.002373 | 0.010689 | 7 | 20 | 30 | 8 |
| 1 | 57 | 1305 | 0.001511 | 0.000066 | 0.000044 | 0.000008 | 84 | 2087 | 3314 | 5227 |
| 2 | 7 | 1501 | 0.019904 | 0.005933 | 0.003798 | 0.001239 | 4 | 11 | 12 | 141 |
| 2 | 8 | 0301 | 0.008890 | 0.003346 | 0.001748 | 0.000983 | 9 | 34 | 63 | 182 |
| 2 | 35 | 0407 | 0.000170 | 0.006589 | 0.000240 | 0.000189 | 862 | 10 | 882 | 945 |
| 2 | 35 | 0802 | 0.000152 | 0.015645 | 0.000181 | 0.000673 | 952 | 3 | 1161 | 278 |
| 2 | 39 | 0407 | 0.000052 | 0.007890 | 0.000123 | 0.000110 | 2066 | 6 | 1615 | 1410 |
| 2 | 44 | 0401 | 0.020677 | 0.003694 | 0.005146 | 0.000546 | 3 | 28 | 8 | 358 |
| 3 | 7 | 1501 | 0.030198 | 0.011575 | 0.006385 | 0.002162 | 2 | 4 | 5 | 66 |
| 11 | 52 | 1502 | 0.001591 | 0.001966 | 0.000160 | 0.002523 | 77 | 77 | 1295 | 48 |
| 24 | 52 | 1502 | 0.000287 | 0.000297 | 0.000085 | 0.012177 | 577 | 609 | 2129 | 4 |
| 26 | 38 | 0402 | 0.005399 | 0.001863 | 0.000221 | 0.000107 | 17 | 84 | 966 | 1432 |
| 29 | 44 | 0701 | 0.015507 | 0.018354 | 0.004269 | 0.000682 | 5 | 1 | 11 | 272 |
| 30 | 13 | 0701 | 0.006485 | 0.003881 | 0.001190 | 0.011410 | 14 | 25 | 112 | 6 |
| 33 | 44 | 0701 | 0.000142 | 0.000870 | 0.000473 | 0.016077 | 1023 | 190 | 440 | 2 |
| 33 | 53 | 0804 | 0.000022 | 0.000592 | 0.007239 | 0.000021 | 3378 | 292 | 3 | 3527 |
| 33 | 58 | 0301 | 0.000236 | 0.000174 | 0.000443 | 0.019323 | 668 | 1003 | 471 | 1 |

Based on the frequencies provided in Table 13 (and the figures would differ if for example, allele-level resolution data were used for HAL-A and/or HLA-B) 18.7%, 10.6%, 4.6%, and 8.2% of the CAU, HIS, AFA, and API populations, respectively, have at least one of the 20 haplotypes. But as discussed above, prospective recipients do not necessarily have to have one of the 20 haplotypes. Rather their tissue type only need contain an HLA-type or allele at each locus that matches the content of the haplotype. For example, the HLA-A1, B8, DRB1*0301 haplotype will be a match to persons whose tissue type contains any of the following haplotypes pairs:

1) HLA-A1, B8, DRB1*0301 plus anything;
2) HLA-A1, B8, DRB1*x plus HLA-Ax, Bx, DRB1*0301; and
3) HLA-A1, Bx, DRB1*0301 plus HLA-Ax, B8, DRB1*x,
4) HLA-A1, Bx, DRB1*x plus HLA-Ax, B8, DRB1*0301;

where x indicates any other the HLA-type or allele at that position. The haplotype frequencies given in Table 12 correspond to 1); 2) through 4) can further raise the likelihood of a match. However, due to the non-random association of From the data in Table 13 it can be seen that the pattern A*01, B*08, DRB1*x does not exist outside of the CAU population in any observed haplotype except A*01, B*08, DRB1*03:01. Additionally the pattern A*01, B*x, DRB1*03:01 does not exist in any observed haplotype except A*01, B*08, DRB1*03:01 (starting from the A*01, B*08, DRB1*03:01 haplotype, it would require two meiotic crossover events to generate this haplotype pattern). Thus haplotype pattern (2) contributes an additional frequency of matching of 0.4% (multiply 1.4% by 2.8%) to the 6.2% frequency of match from donor and prospective CAU recipient sharing the A*01, B*08, DRB1*03:01 haplotype. Haplotype pattern (3) is not expected to occur. Haplotype pattern (4) contributes an additional frequency of matching of 0.2%, 0.01%, 0.001%, and 0.01% to the frequency of match from donor and prospective CAU, HIS, AFA, and API recipients sharing the A*01, B*08, DRB1*03:01 haplotype, respectively. Thus, the expected frequency of matching this haplotype is 6.8% for the CAU population but does not appreciably change for the other three populations. And in all cases the frequency due to haplotype matching, rather than matching to the full tissue type, provides a reasonable estimate of the likelihood of matching. This also illustrates that the primary gain in matching likelihood comes from avoiding the need to match two antigens at each locus. This pattern is a consequence of the substantial linkage disequilibrium within the MHC. That tissue type matching will primarily arise from a shared haplotype demonstrates the efficiency of the homozygous donor approach.

TABLE 14

Frequencies of HLA-A2, B7, DRB1*15:01 related haplotypes

| Haplotype Pattern | HLA-A | HLA-B | HLA-DRB1 | CAU (%) | HIS (%) | AFA (%) | API (%) |
|---|---|---|---|---|---|---|---|
| (1) | 02 | 07 | 15:01 | 2.0 | 0.6 | 0.4 | 0.1 |
| (2) | 02 | 07 | X | 0.8 | 0.1 | 0.2 | 0.1 |
|  | X | X | 15:01 | 7.1 | 2.6 | 1.1 | 4.7 |
| (3) | 02 | X | 15:01 | 1.1 | 0.1 | 0.1 | 1.5 |
|  | X | 07 | X | 7.3 | 2.1 | 2.9 | 1.9 |
| (4) | 02 | X | X | 17.1 | 15.7 | 7.5 | 11.1 |
|  | X | 07 | 15:01 | 4.7 | 2.3 | 1.3 | 0.2 |

A similar analysis of the contribution to the likelihood of a match from complementary, non-matching haplotypes, as done for A*01, B*08, DRB1*03:01, was also done for A*02, B*07, DRB1*15:01 (Table 14). As A2 and B7 are the most common types for the HLA-A and -B loci in the CAU population it appeared possible that they would be represented on a more diverse set of haplotypes. Also, as the CAU population is the least genetically diverse of the four subpopulations, the frequency of individual haplotypes will be on average higher and the contribution of complementary, non-matching haplotypes to the overall likelihood of a match will be generally greater. From the data in Table 13 it is immediately apparent that there are observed haplotypes matching each of the haplotype patterns for all for subpopulations. The additional matching frequency for the tissue types with the haplotype pattern A*02, B*07, DRB1*x plus A*x, B*x, DRB1*15:01 was 0.06%, 0.003%, 0.002%, and 0.005% for matching with prospective CAU, HIS, AFA, and API recipients, respectively. The additional matching frequency for the tissue types with the haplotype pattern A*02, B*x, DRB1*15:01 plus A*x, B*07, DRB1*x was 0.08%, 0.002%, 0.003%, and 0.03% for matching with prospective CAU, HIS, AFA, and API recipients, respectively. The additional matching frequency for the tissue types with the haplotype pattern A*02, B*x, DRB1*x plus A*x, B*07, DRB1*15:01 was 0.8%, 0.4%, 0.1%, and 0.02% for matching with prospective CAU, HIS, AFA, and API recipients, respectively. Thus the expected frequency of having a tissue type matching this haplotype is 2.9% for the CAU population versus 2.0% for having the same haplotype. The same comparisons for HIS, AFA, and API are 1.0 versus 0.6, 0.5 versus 0.4, and 0.16 versus 0.1, respectively. Thus even under favorable circumstances the additional matching frequency contributed by complementary, non-matching haplotypes is only a fraction of that due to having the matching haplotype.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A library of HLA homozygous induced pluripotent stem cell (iPS) lines, the library comprising:
   at least 20 different iPS cell lines homozygous for alleles at HLA-A, -B, and -DR loci, each cell line expressing a different homozygous haplotype, wherein the at least 20 iPS cell lines each have a haplotype selected from:

| HLA-A* | HLA-B* | HLA-DRB1* |
|---|---|---|
| 01:01 | 08:01 | 03:01 |
| 03:01 | 07:02 | 15:01 |
| 02:01 | 44:02 | 04:01 |
| 02:01 | 07:02 | 15:01 |
| 29:02 | 44:03 | 07:01 |
| 02:01 | 15:01 | 04:01 |
| 01:01 | 57:01 | 07:01 |
| 03:01 | 35:01 | 01:01 |
| 02:01 | 40:01 | 13:02 |
| 30:01 | 13:02 | 07:01 |
| 02:01 | 08:01 | 03:01 |
| 02:01 | 57:01 | 07:01 |
| 24:02 | 07:02 | 15:01 |
| 11:01 | 35:01 | 01:01 |
| 33:01 | 14:02 | 01:02 |
| 23:01 | 44:03 | 07:01 |
| 01:01 | 07:02 | 15:01 |
| 02:01 | 15:01 | 13:01 |
| 02:01 | 13:02 | 07:01 |
| 31:01 | 40:01 | 04:04 |
| 25:01 | 18:01 | 15:01 |
| 02:01 | 44:03 | 07:01 |
| 02:01 | 44:02 | 13:01 |
| 02:01 | 44:02 | 01:01 |
| 01:01 | 08:01 | 15:01 |
| 03:01 | 07:02 | 01:01 |
| 02:01 | 44:02 | 15:01 |
| 02:01 | 51:01 | 11:01 |
| 26:01 | 38:01 | 04:02 | wherein each of the iPS cell lines has been reprogrammed into pluripotentiality by means of non-endogenous transcription factors.

2. The library of claim 1, wherein said at least 20 different PS cell lines are homozygous additionally for alleles at one of more loci selected from HLA-C, -DQ, and DP.

3. The library of claim 1 wherein at least 15 of the 20 different iPS cell lines carries a haplotype comprising at least two alleles for a type selected from A1, A2, A3, A24, A29, A33, B7, B8, B35, B39, B44, B48, B52, B60, DR2, DR3, DR4, DR7, DR8, DR9, DR11, DR12, DR13, and DR15.

4. The library of claim 1, wherein each haplotype is compatible with a tissue type of a fraction of the individuals in a defined population and the sum of fractions for all of the haplotypes in the library is at least 5, 10, 15, 25, 30, 35, 40, 45, 50, 55, or 60 percent of the defined population.

5. The library of claim 4, wherein the library comprises all haplotypes occurring at a frequency of >2%, >3% or >4% in the defined population.

6. The library of claim 4 wherein the library comprises ≥50%, ≥60%, ≥70%, ≥80%, ≥90%, or ≥95% of all haplotypes occurring at a frequency of >1%, >0.9%, >0.8%, >0.7%, >0.6%, >0.5%, >0.4%, >0.3%, >0.2%, >0.1%, >0.09%, >0.08, >0.07%, >0.06% or >0.05% in the defined population.

7. The library of claim 4 wherein said defined population is defined by geographic origin, geographic location, ethnic background, or a combination thereof.

8. The library of claim 7, wherein the defined geographical location is a state, a country, a continent, or a region thereof.

9. The library of claim 7, wherein the defined geographical location is the US or Japan.

10. The library of claim 1, wherein the at least 20 different PS cell lines are derived from cord blood.

11. The library of claim 1 wherein homozygous haplotypes expressed by the at least 20 different iPSC lines comprise

| | | |
|---|---|---|
| A*01:01 | B*08:01 | DRB1*03:01 |
| A*01:01 | B*35:02 | DRB1*11:04 |
| A*01:01 | B*57:01 | DRB1*07:01 |
| A*01:01 | B*57:01 | DRB1*13:05 |
| A*02:01 | B*07:02 | DRB1*15:01 |
| A*02:01 | B*08:01 | DRB1*03:01 |
| A*02:01 | B*35:01 | DRB1*04:07 |
| A*02:06 | B*35:12 | DRB1*08:02 |
| A*02:01 | B*39:01 | DRB1*04:07 |
| A*02:01 | B*44:02 | DRB1*04:01 |
| A*03:01 | B*07:02 | DRB1*15:01 |
| A*11:02 | B*52:01 | DRB1*15:02 |
| A*24:02 | B*52:01 | DRB1*15:02 |
| A*26:01 | B*38:01 | DRB1*04:02 |
| A*26:01 | B*38:01 | DRB1*13:02 |
| A*29:02 | B*44:03 | DRB1*07:01 |
| A*30:01 | B*13:02 | DRB1*07:01 |
| A*33:03 | B*044:03 | DRB1*07:01 |
| A*33:03 | B*53:01 | DRB1*08:04 |
| A*33:03 | B*58:01 | DRB1*03:01. |

12. A method of producing the library of HLA homozygous induced pluripotent stem cell (iPS) lines of claim 1 comprising:
 screening cord blood units donated to a cord blood repository for:
 a) genetic, cytogenetic and other genomic and chromosomal abnormalities
 b) history and markers of exposure to infectious diseases
 c) homozygosity for all of HLA-A, -B, -C, and -Dr loci;
 isolating white blood cells from the cord blood units negative for genetic defects, exposure to infectious diseases, and transposons, and homozygous for HLA-A, -B, -C, and -Dr,
 causing the white blood cells to express Oct-4, Sox-2, Klf-4, and c-Myc to form iPS cells;
 culturing and cloning the iPSC to produce a population of cloned iPS cells homozygous for their HLA-A, -B, -C, and -DR haplotypes;
 characterizing the genotype of the iPSC by typing of HLA markers beyond the A,B,C and DR loci to include additional class I, II and III genes;
 screening the cells from iPSC clones for the presence of chromosomal aberrations and evidences of genetic instability and
 cryoprotecting and storing the cloned population of iPSC.

13. The method of claim 12, wherein the causing step includes using vectors capable of inducing the target white blood cells to express the exogenous transcription factors Oct-4, Sox-2, Klf-4, and c-Myc.

14. The method of claim 12, wherein method further comprises isolating hematopoietic CD34+ cells from the cord blood prior to the causing step.

15. A method for providing differentiated cells derived from the library of HLA homozygous induced pluripotent stem cell (PS) lines of claim 1 to a subject in need thereof comprising:
 determining the HLA haplotype for HLA-A, -B, -C and -DR of the subject;
 selecting an iPSC line from the library of claim 1 which contains a match at all of HLA-A, -B, -C, and -DR loci with the subject's HLA phenotype for those loci;
 differentiating the iPSC into a cell type needed by the subject; and
 providing the differentiated cells to the subject.

16. The method of claim 15, wherein the step of providing the differentiated cells to the subject comprises providing the differentiated cells to the subject's medical provider.

17. The method of claim 15 further comprising expanding and fully differentiating the iPS cells into a differentiated cell type and ensuring the disappearance of the pluripotent cells and inducing vectors, and as the genetic stability of the differentiated cells.

18. The library of claim 1 wherein the at least 20 different iPS cell lines are homozygous for alleles at MICA and MICB loci, wherein the haplotype differences are at an HLA-A, -B, or -DR locus.

19. The library of claim 1 wherein the said at least 20 different PS cell lines are homozygous for alleles at HLA-F and -DPB3 loci wherein the haplotype differences are at an HLA-A, -B, or -DR locus.

20. The method of claim 17, wherein the differentiated cell type is selected from neural cells, myocardial muscle cells, and insulin-producing cells.

\* \* \* \* \*